United States Patent [19]

Matthews et al.

[11] Patent Number: 5,777,162
[45] Date of Patent: Jul. 7, 1998

[54] INTERMEDIATES FOR THE PREPARATION OF FUNGICIDES

[75] Inventors: Ian Richard Matthews, Wokingham; Christopher Richard Ayles Godfrey, Great Hollands; John Martin Clough, Marlow, all of England

[73] Assignee: Zeneca Limited, London, England

[21] Appl. No.: 748,088

[22] Filed: Nov. 12, 1996

Related U.S. Application Data

[62] Division of Ser. No. 211,390, Aug. 18, 1994.

[30] Foreign Application Priority Data

Sep. 30, 1991 [GB] United Kingdom ............... 9120771
Oct. 29, 1991 [GB] United Kingdom ............... 9122875
Sep. 9, 1992 [WO] WIPO ..................... PCT/GB92/01644

[51] Int. Cl.[6] ............... C07C 233/00; C07C 235/00; C07C 249/04
[52] U.S. Cl. ............... 564/167; 560/60; 560/27; 548/163; 548/170; 548/187; 548/194; 548/491; 548/510; 548/953; 558/245; 558/248; 558/270; 558/271; 558/272; 558/277; 546/301; 546/309; 546/226; 564/163; 544/298; 544/322; 544/336; 544/59; 544/158; 544/172; 549/228; 549/438; 549/439; 504/235; 504/239; 504/242; 504/254; 504/266; 504/267; 504/268; 504/296; 504/306; 504/307; 504/309; 504/314; 504/315; 504/209; 504/221; 504/226
[58] Field of Search ............... 564/163, 167

[56] References Cited

U.S. PATENT DOCUMENTS

| | | | |
|---|---|---|---|
| 3,751,450 | 8/1973 | Fischer et al. | 560/130 |
| 4,822,908 | 4/1989 | Karbach et al. | 560/60 |
| 4,895,974 | 1/1990 | Crowley | 560/60 |
| 4,952,720 | 8/1990 | Schuetz et al. | 560/106 |
| 5,192,357 | 3/1993 | Cliff et al. | 504/315 |
| 5,286,894 | 2/1994 | Bushell et al. | 560/55 |
| 5,315,025 | 5/1994 | Bushell et al. | 560/60 |
| 5,334,602 | 8/1994 | Lotz et al. | 514/317 |
| 5,416,068 | 5/1995 | Grammenos et al. | 504/378 |
| 5,416,110 | 5/1995 | Wingert et al. | 514/488 |
| 5,438,059 | 8/1995 | Clough et al. | 514/256 |
| 5,446,067 | 8/1995 | Benoit et al. | 514/640 |
| 5,516,932 | 5/1996 | Beller et al. | 560/104 |

FOREIGN PATENT DOCUMENTS

| | | |
|---|---|---|
| 20590/92 | 1/1993 | Australia . |
| 0 307 103 | 3/1989 | European Pat. Off. . |
| 0 310 954 | 4/1989 | European Pat. Off. . |
| 0 398 692 | 11/1990 | European Pat. Off. . |
| 1363788 | 8/1974 | United Kingdom . |

OTHER PUBLICATIONS

N. Latif et al., "A simple One–Step Synthesis of 3,4–Dihydro–4–phenacyl–2H–1,3–benzoxazin–2–ones," *Synthesis*, Mar. 1988, pp. 246–248.

*Primary Examiner*—Johann Richter
*Assistant Examiner*—Laura L. Stockton
*Attorney, Agent, or Firm*—Joseph R. Snyder

[57] ABSTRACT

Described herein are compounds of Formula (XX) and Formula (XXIV), shown below, and processes of making same.

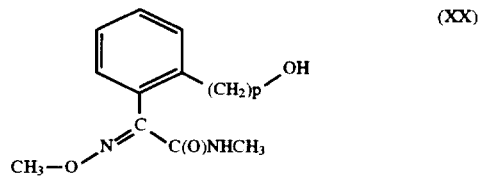

(XX)

wherein p is 0

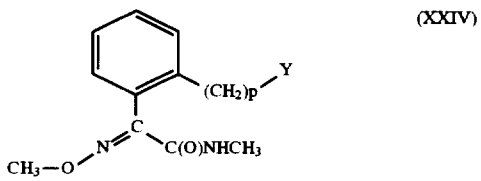

(XXIV)

wherein p is 1, and Y is chlorine or bromine.

6 Claims, No Drawings

5,777,162

INTERMEDIATES FOR THE PREPARATION OF FUNGICIDES

This application is a divisional of application Ser. No. 08/211,390, filed Aug. 18, 1994.

The present invention relates to carbonate, carbamate, thiocarbonate, dithiocarbonate and thiocarbamate derivatives that are useful as fungicides, to processes for preparing them, to compositions containing them and to methods of using them to combat fungi, especially fungal infections of plants.

According to the present invention there is provided a compound having the general formula (I), wherein W is $CH_3O.CH=CCO_2CH_3$, $CH_3ON=CCONR^3R^4$ or $CH_3ON=CCO_2CH_3$ and stereoisomers thereof; n is 0 or 1; X is oxygen or sulphur; Z is oxygen, sulphur or $NR^1$; $R^1$ is hydrogen or alkyl optionally substituted with halogen, $C_{1-6}$ alkoxy, $C_{2-6}$ alkenyl, $C_{2-6}$ alkynyl, $C_{3-6}$ cycloalkyl or aryl; $R^2$ is alkyl, haloalkyl, alkenyl, alkynyl, alkoxycarbonyl $(C_{1-4})$alkyl, optionally substituted aryl, optionally substituted heteroaryl, optionally substituted aryl$(C_{1-4})$alkyl, optionally substituted heteroaryl$(C_{1-4})$alkyl, optionally substituted aryloxy$(C_{1-4})$-alkyl, optionally substituted heteroaryloxy$(C_{1-4})$alkyl, optionally substituted aryloxy$(C_{2-4})$alkenyl, optionally substituted heteroaryloxy-$(C_{2-4})$alkenyl, optionally substituted aryl$(C_{2-4})$alkenyl, optionally substituted heteroaryl$(C_{2-4})$alkenyl, optionally substituted arylcarbonyl-$(C_{1-4})$alkyl, optionally substituted heteroarylcarbonyl$(C_{1-4})$alkyl, optionally substituted aryloxycarbonyl-$(C_{1-4})$alkyl, optionally substituted heteroaryloxycarbonyl$(C_{1-4})$alkyl or $—COR^5$; or $R^1$ and $R^2$ together form an optionally substituted 4-, 5- or 6-membered heterocyclic ring system; $R^3$ and $R^4$ are independently hydrogen or methyl; and $R^5$ is optionally substituted heteroaryl or optionally substituted aryl; provided that when W is $CH_3O.CH=CCO_2CH_3$, n is 1 and X and Z are both oxygen then $R^2$ is not optionally substituted aryl.

Because the double bond of the propenoate, oxyiminoacetamide or oxyiminoacetate group is unsymmetrically substituted, the compounds of the invention may be obtained in the form of mixtures of (E)- and (Z)-geometric isomers. However, these mixtures can be separated into individual isomers, and this invention embraces such isomers and mixtures thereof in all proportions including those which consist substantially of the (Z)-isomer and those which consist substantially of the (E)-isomer. The (E)-isomers are the more fungicidally active and form a preferred embodiment of the invention.

When W is $CH_3ON=CCONR^3R^4$ it is preferred that $R^3$ is hydrogen and that $R^4$ is methyl.

Aryl is preferably phenyl.

Heteroaryl includes 5- and 6-membered aromatic rings containing one or more heteroatoms selected from the list comprising oxygen, sulphur and nitrogen and can be fused to benzenoid ring systems. Examples of heteroaryl are pyridinyl, pyrimidinyl, pyridazinyl, pyrazinyl, triazinyl, furyl, thienyl, pyrrolyl, pyrazolyl, imidazolyl, triazolyl, oxazolyl, isoxazolyl, thiazolyl, isothiazolyl, quinolinyl, isoquinolinyl, cinnolinyl, quinazolinyl, quinoxalinyl, indolinyl, isoindolinyl, benzofuranyl, benzothiophenyl and benzimidazolinyl.

Examples of the heterocyclic ring system which can be formed by $R^1$ and $R^2$ are pyrrole, pyrrolidine, thiomorpholine, indoline, azetidine, indole, isoindole, imidazole, piperidine, morpholine, benzimidazole and pyrazole. These ring systems are unsubstituted, or substituted as for heteroaryl.

Substitutents which may be present in optionally substituted aryl and heteroaryl moieties include one or more of the following: halo, hydroxy, mercapto, $C_{1-4}$ alkyl (especially methyl and ethyl), $C_{2-4}$ alkenyl (especially allyl), $C_{2-4}$ alkynyl (especially propargyl), $C_{1-4}$ alkoxy (especially methoxy), $C_{2-4}$ alkenyloxy (especially allyloxy), $C_{2-4}$ alkynyloxy (especially propargyloxy), halo$(C_{1-4})$alkyl (especially trifluoromethyl), halo$(C_{1-4})$alkoxy (especially trifluoromethoxy), $C_{1-4}$ alkylthio (especially methylthio), hydroxy$(C_{1-4})$alkyl, $C_{1-4}$ alkoxy$(C_{1-4})$alkyl, $C_{3-6}$ cycloalkyl, $C_{3-6}$ cycloalkyl$(C_{1-4})$alkyl, optionally substituted methylenedioxy (especially optionally substituted with fluorine or $C_{1-4}$ alkyl), optionally substituted aryl (especially optionally substituted phenyl), optionally substituted heteroaryl (especially optionally substituted pyridyl or pyridinyl), optionally substituted heterocyclyl (especially optionally substituted pyrrolidine), optionally substituted aryloxy (especially optionally substituted phenoxy), optionally substituted heteroaryloxy (especially optionally substituted pyridyloxy or pyrimidinyloxy), optionally substituted aryl$(C_{1-4})$alkyl (especially optionally substituted benzyl, optionally substituted phenethyl and optionally substituted phenyl n-propyl) in which the alkyl moiety is optionally substituted with hydroxy, optionally substituted heteroaryl-$(C_{1-4})$alkyl (especially optionally substituted pyridyl- or pyrimidinyl-$(C_{1-4})$alkyl), optionally substituted aryl$(C_{2-4})$alkenyl (especially optionally substituted phenylethenyl), optionally substituted heteroaryl$(C_{2-4})$alkenyl (especially optionally substituted pyridylethenyl or pyrimidinylethenyl), optionally substituted aryl$(C_{1-4})$alkoxy (especially optionally substituted benzyloxy), optionally substituted heteroaryl$(C_{1-4})$alkoxy (especially optionally substituted pyridyl- or pyrimidinyl$(C_{1-4})$alkoxy), optionally substituted aryloxy$(C_{1-4})$alkyl (especially phenoxymethyl), optionally substituted heteroaryloxy$(C_{1-4})$alkyl (especially optionally substituted pyridyloxy- or pyrimidinyloxy$(C_{1-4})$alkyl), acyloxy (including $C_{1-4}$ alkanoyloxy (especially acetyloxy) and benzoyloxy), cyano, thiocyanato, nitro, $—NR'R"$, $—NHCOR'$, $—NHCONR'R"$, $—CONR'R"$, $—COOR'$, $—OSO_2R'$, $—SO_2R'$, $—COR'$, $—CR'=NR"$ or $—N=CR'R"$ in which $R'$ and $R"$ are independently hydrogen, $C_{1-4}$ alkyl, $C_{1-4}$alkoxy, $C_{1-4}$ alkylthio, $C_{3-6}$ cycloalkyl, $C_{3-6}$ cycloalkyl$(C_{1-4})$alkyl, phenyl or benzyl, the phenyl and benzyl groups being optionally substituted with halogen, $C_{1-4}$ alkyl or $C_{1-4}$ alkoxy; when $R'$ and $R"$ are in $CONR'R"$ they can together form a 5- or 6-membered heterocyclic ring (for example a pyrrole, imidazole, pyrrolidine, piperidine or morpholine ring); or two substituents, when they are in adjacent positions on the aryl or heteroaryl ring can join to form a fused aliphatic ring (especially to form a fused 6-membered carbon aliphatic ring).

Substituents which may be present in the aryl or heteroaryl rings of any of the foregoing substituents include one or more of the following: halo, hydroxy, mercapto, $C_{1-4}$ alkyl, $C_{2-4}$ alkenyl, $C_{2-4}$ alkynyl, $C_{1-4}$ alkoxy, $C_{2-4}$ alkenyloxy, $C_{2-4}$ alkynyloxy, halo$(C_{1-4})$alkyl, halo$(C_{1-4})$alkoxy, $C_{1-4}$ alkylthio, hydroxy$(C_{1-4})$alkyl, $C_{1-4}$ alkoxy$(C_{1-4})$alkyl, $C_{3-6}$ cycloalkyl, $C_{3-6}$ cycloalkyl$(C_{1-4})$alkyl, alkanoyloxy, benzoyloxy, cyano, thiocyanato, nitro, $—NR'R"$, $—NHCOR'$, $—NHCONR'R"$, $—CONR'R"$, $—COOR'$, $—SO_2R'$, $—OSO_2R'$, $—COR'$, $—CR'=NR"$ or $—N=CR'R"$ in which $R'$ and $R"$ have the meanings given above.

All alkyl moieties and the alkyl moiety of alkoxy preferably contain from 1 to 6, more preferably from 1 to 4, carbon atoms. They can be in the form of straight or branched chains, for example methyl, ethyl, n- or iso-propyl, or n-, sec-, iso- or tert-butyl.

Alkenyl and alkynyl moieties preferably contain from 2 to 6, more preferably from 2 to 4, carbon atoms. They can be in the form of straight or branched chains, and the alkenyl moieties, where appropriate, may have either the (E)- or (Z)-configuration. Examples are vinyl, allyl and propargyl.

Halogen is typically fluorine, chlorine or bromine.

In one aspect the present invention provides a compound of formula (I) wherein W is $CH_3O.CH=CCO_2CH_3$.

In another aspect the present invention provides a compound of formula (I) wherein $R^2$ optionally substituted phenyl (especially phenyl substituted by halogen, hydroxy, alkyl, haloalkyl, alkoxy, haloalkoxy, alkylthio, nitro or cyano).

In a further aspect the present invention provides a compound of formula (I) wherein Z is $NR^1$ (wherein $R^1$ is hydrogen, alkyl (especially methyl or ethyl) or alkyl substituted by alkenyl or alkynyl (thus forming, for example, an allyl or propargyl group)).

In a still further aspect the present invention provides a compound of formula (XI) wherein $R^1$ is hydrogen or $C_{1-4}$ alkyl (especially methyl or ethyl); and $R^2$ is phenyl optionally substituted with halogen (for example fluorine or chlorine), hydroxy, $C_{1-6}$ alkyl (such as methyl or ethyl), $C_{1-6}$ haloalkyl (for example trifluoromethyl), $C_{1-6}$ alkoxy (such as methoxy or ethoxy), $C_{1-6}$ haloalkoxy (for example trifluoromethoxy), $C_{1-6}$ alkylthio (such as methylthio), nitro or cyano.

In another aspect the present invention provides a compound of general formula (II), wherein n is 0 or 1; X is oxygen or sulphur; $R^1$ is hydrogen or $C_{1-4}$ alkyl (especially methyl or ethyl); and $R^2$ is phenyl($C_{1-4}$)alkyl (especially benzyl), benzoyl or phenyl (optionally substituted by halogen (especially chlorine and fluorine), nitro, halo($C_{1-4}$)alkyl (especially trifluoromethyl), $C_{1-4}$ alkoxy (especially methoxy) or $C_{1-4}$ alkylthio (especially methylthio)).

In a further aspect the present invention provides a compound of general formula (I) wherein W is $CH_3ON=CCONHCH_3$ or, preferably, $CH_3O.CH=CCO_2CH_3$; n is 0 or 1; X is sulphur or, preferably, oxygen; Z is oxygen, sulphur or, preferably, $NR^1$; $R^1$ is hydrogen, $C_{1-4}$ alkyl (especially methyl, ethyl or n-propyl), $C_{1-4}$ haloalkyl (especially $CH_2CHF_2$) or $C_{2-4}$ alkynyl (especially $CH_2C\equiv CH$); $R^2$ is phenyl (optionally substituted by halogen (especially fluorine or chlorine), nitro, cyano, $C_{1-4}$ alkyl (especially methyl), $C_{1-4}$ alkoxy (especially methoxy or ethoxy), $C_{1-4}$ alkylthio (especially methylthio), $C_{1-4}$ haloalkyl (especially trifluoromethyl), $CONH_2$, $CSNH_2$, $C_{1-4}$ alkylsulphonyl (especially methylsulphonyl), methylenedioxy or $C_{1-4}$ alkoxycarbonyl (especially methoxy- or ethoxy-carbonyl)), phenyl($C_{1-4}$) alkyl (especially benzyl), benzoyl, $C_{2-4}$ alkenyl (especially allyl), pyridinyl (optionally substituted by halogen (especially fluorine or chlorine), $C_{1-4}$ alkoxy (especially methoxy), pyrazinyl, pyrimidinyl (optionally substituted by nitro), pyridazinyl, benzothiazolyl (optionally substituted by $C_{1-4}$ alkoxy (especially methoxy)), indolyl, thiazolyl (optionally substituted by $C_{1-4}$ alkyl (especially methyl)), or benzoxazolyl (optionally substituted by halogen (especially chlorine)); provided that when W is $CH_3O.CH=CCO_2CH_3$, n is 1 and X and Z are both oxygen then $R^2$ is not optionally substituted aryl.

In a still further aspect the present invention provides a compound of general formula (I) wherein W is $CH_3O.CH=CCO_2CH_3$; n is 0 or 1; X is oxygen or sulphur; Z is $NR^1$; and $R^1$ and $R^2$ together form a pyrrole, indole, isoindole, imidazole, pyrrolidine, piperidine, indoline, morpholine, thiomorpholine, benzimidazole or pyrazole ring.

The present invention is illustrated by compounds of formula I which are listed in Tables 1 to 133. Compounds in Table 1 are of general formula (II) wherein Z is $NR^1$ and $R^1$ is hydrogen, X is oxygen, n is 1 and $R^2$ is as given below.

TABLE 1

| Compound No. | $R^2$ |
|---|---|
| 1 | $C_6H_5CO$ |
| 2 | $3\text{-}CF_3\text{---}C_6H_4$ |
| 3 | $2\text{-}F\text{---}C_6H_4$ |
| 4 | $C_6H_5CH_2$ |
| 5 | $C_6H_5$ |
| 6 | $3\text{-}NO_2\text{---}C_6H_4$ |
| 7 | $3\text{-}CH_3O\text{---}C_6H_4$ |
| 8 | $3\text{-}F\text{---}C_6H_4$ |
| 9 | $4\text{-}NO_2\text{---}C_6H_4$ |
| 10 | $3\text{-}CH_3S\text{---}C_6H_4$ |
| 11 | $4\text{-}Cl\text{---}C_6H_4$ |
| 12 | $2\text{-}Cl\text{---}C_6H_4$ |
| 13 | $4\text{-}F\text{---}C_6H_4$ |
| 14 | $3\text{-}Cl\text{---}C_6H_4$ |
| 15 | $2\text{-}NO_2\text{---}C_6H_4$ |
| 16 | $2\text{-}CH_3O\text{---}C_6H_4$ |
| 17 | $4\text{-}CH_3O\text{---}C_6H_4$ |
| 18 | $2\text{-}CF_3\text{---}C_6H_4$ |
| 19 | $4\text{-}CF_3\text{---}C_6H_4$ |
| 20 | allyl |
| 21 | $2\text{-}CH_3S\text{---}C_6H_4$ |
| 22 | $4\text{-}CH_3S\text{---}C_6H_4$ |
| 23 | $2,6\text{-}F_2\text{---}C_6H_3$ |
| 24 | $2,4\text{-}F_2\text{---}C_6H_3$ |
| 25 | $2,3\text{-}F_2\text{---}C_6H_3$ |
| 26 | $3,5\text{-}F_2\text{---}C_6H_3$ |
| 27 | $2,5\text{-}F_2\text{---}C_6H_3$ |
| 28 | $3,4\text{-}F_2\text{---}C_6H_3$ |
| 29 | $2\text{-cyano-}C_6H_4$ |
| 30 | $3\text{-cyano-}C_6H_4$ |
| 31 | $4\text{-cyano-}C_6H_4$ |
| 32 | $2\text{-}CH_3O\text{-pyridin-5-yl}$ |
| 33 | $2\text{-}CH_3O_2C\text{---}C_6H_4$ |
| 34 | $3\text{-}CH_3O_2C\text{---}C_6H_4$ |
| 35 | $4\text{-}CH_3O_2C\text{---}C_6H_4$ |
| 36 | $2\text{-}C_2H_5O_2C\text{---}C_6H_4$ |
| 37 | $3\text{-}C_2H_5O_2C\text{---}C_6H_4$ |
| 38 | $4\text{-}C_2H_5O_2C\text{---}C_6H_4$ |
| 39 | $2\text{-}CSNH_2\text{---}C_6H_4$ |
| 40 | $3\text{-}CSNH_2\text{---}C_6H_4$ |
| 41 | $4\text{-}CSNH_2\text{---}C_6H_4$ |
| 42 | $2\text{-}CONH_2\text{---}C_6H_4$ |
| 43 | $3\text{-}CONH_2\text{---}C_6H_4$ |
| 44 | $4\text{-}CONH_2\text{---}C_6H_4$ |
| 45 | $2\text{-}SO_2CH_3\text{---}C_6H_4$ |
| 46 | $3\text{-}SO_2CH_3\text{---}C_6H_4$ |
| 47 | $2\text{-}C_2H_5O\text{---}C_6H_4$ |
| 48 | $3\text{-}C_2H_5O\text{---}C_6H_4$ |
| 49 | $4\text{-}C_2H_5O\text{---}C_6H_4$ |
| 50 | $2,6\text{-}(CH_3O)_2\text{---}C_6H_3$ |
| 51 | $2,5\text{-}(CH_3O)_2\text{---}C_6H_3$ |
| 52 | $2,4\text{-}(CH_3O)_2\text{---}C_6H_3$ |
| 53 | $2,3\text{-}(CH_3O)_2\text{---}C_6H_3$ |
| 54 | $3,5\text{-}(CH_3O)_2\text{---}C_6H_3$ |
| 55 | $3,4\text{-}(CH_3O)_2\text{---}C_6H_3$ |
| 56 | $2\text{-}CH_3\text{---}C_6H_4$ |
| 57 | $3\text{-}CH_3\text{---}C_6H_4$ |
| 58 | $4\text{-}CH_3\text{---}C_6H_4$ |
| 59 | $3,4\text{-methylenedioxy-}C_6H_3$ |
| 60 | pyridin-2-yl |
| 61 | pyridin-3-yl |
| 62 | pyridin-4-yl |
| 63 | $2\text{-}CH_3O\text{-pyridin-3-yl}$ |
| 64 | $4\text{-}CH_3O\text{-pyridin-3-yl}$ |
| 65 | $5\text{-}CH_3O\text{-pyridin-3-yl}$ |
| 66 | $6\text{-}CH_3O\text{-pyridin-2-yl}$ |
| 67 | $5\text{-}CH_3O\text{-pyridin-2-yl}$ |

TABLE 1-continued

| Compound No. | R² |
|---|---|
| 68 | 4-CH₃O-pyridin-2-yl |
| 69 | 3-CH₃O-pyridin-2-yl |
| 70 | 2-CH₃O-pyridin-4-yl |
| 71 | 3-CH₃O-pyridin-4-yl |
| 72 | pyrazinyl |
| 73 | pyrimidin-2-yl |
| 74 | pyrimidin-4-yl |
| 75 | pyrimidin-5-yl |
| 76 | 2,6-Cl₂-pyridin-3-yl |
| 77 | 2,6-F₂-pyridin-3-yl |
| 78 | 2,6-(CH₃O)₂-pyridin-3-yl |
| 79 | pyridazin-3-yl |
| 80 | pyridazin-4-yl |
| 81 | 2-benzothiazolyl |
| 82 | 5-indolyl |
| 83 | 4-methoxybenzothiazol-2-yl |
| 84 | thiazol-2-yl |
| 85 | 4-methylthiazol-2-yl |
| 86 | 5-nitropyrimidin-2-yl |
| 87 | 3-nitropyrimidin-2-yl |
| 88 | 5-chlorobenzoxazol-2-yl |
| 89 | 2-Cl-pyridin-3-yl |
| 90 | 4-Cl-pyridin-3-yl |
| 91 | 5-Cl-pyridin-3-yl |
| 92 | 6-Cl-pyridin-2-yl |
| 93 | 5-Cl-pyridin-2-yl |
| 94 | 4-Cl-pyridin-2-yl |
| 95 | 3-Cl-pyridin-2-yl |
| 96 | 2-F-pyridin-3-yl |
| 97 | 4-F-pyridin-3-yl |
| 98 | 5-F-pyridin-3-yl |
| 99 | 6-F-pyridin-2-yl |
| 100 | 5-F-pyridin-2-yl |
| 101 | 4-F-pyridin-2-yl |
| 102 | 3-F-pyridin-2-yl |
| 103 | 4-SO₂CH₃—C₆H₄ |
| 104 | 4-F-3-Cl—C₆H₃ |
| 105 | 4-F-3-NO₂—C₆H₃ |
| 106 | 2-F-3-NO₂—C₆H₃ |
| 107 | 4-F-2-Cl—C₆H₃ |
| 108 | 3-F-2-Cl—C₆H₃ |
| 109 | 3-F-4-Cl—C₆H₃ |
| 110 | 3-F-5-Cl—C₆H₃ |
| 111 | 2-F-3-Cl—C₆H₃ |
| 112 | 2-F-4-Cl—C₆H₃ |
| 113 | 2-F-5-Cl—C₆H₃ |
| 114 | 2-F-6-Cl—C₆H₃ |
| 115 | 3-F-6-Cl—C₆H₃ |
| 116 | 2,6-Cl₂—C₆H₃ |
| 117 | 2,5-Cl₂—C₆H₃ |
| 118 | 2,4-Cl₂—C₆H₃ |
| 119 | 2,3-Cl₂—C₆H₃ |
| 120 | 3,5-Cl₂—C₆H₃ |
| 121 | 3,4-Cl₂—C₆H₃ |

TABLE 2

Table 2 comprises 121 compounds of general formula (II) wherein Z is $NR^1$ and $R^1$ is methyl, X is oxygen, n is 1 and $R^2$ is as listed in Table 1.

TABLE 3

Table 3 comprises 121 compounds of general formula (II) wherein Z is $NR^1$ and $R^1$ is ethyl, X is oxygen, n is 1 and $R^2$ is as listed in Table 1.

TABLE 4

Table 4 comprises 121 compounds of general formula (II) wherein Z is $NR^1$ and $R^1$ is n-propyl, X is oxygen, n is 1 and $R^2$ is as listed in Table 1.

TABLE 5

Table 5 comprises 121 compounds of general formula (II) wherein Z is $NR^1$ and $R^1$ is $CH_2CHF_2$, X is oxygen, n is 1 and $R^2$ is as listed in Table 1.

TABLE 6

Table 6 comprises 121 compounds of general formula (II) wherein Z is $NR^1$ and $R^1$ is hydrogen, X is sulphur, n is 1 and $R^2$ is as listed in Table 1.

TABLE 7

Table 7 comprises 121 compounds of general formula (II) wherein Z is $NR^1$ and $R^1$ is methyl, X is sulphur, n is 1 and $R^2$ is as listed in Table 1.

TABLE 8

Table 8 comprises 121 compounds of general formula (II) wherein Z is $NR^1$ and $R^1$ is ethyl, X is sulphur, n is 1 and $R^2$ is as listed in Table 1.

TABLE 9

Table 9 comprises 121 compounds of general formula (II) wherein Z is $NR^1$ and $R^1$ is n-propyl, X is sulphur, n is 1 and $R^2$ is as listed in Table 1.

TABLE 10

Table 10 comprises 121 compounds of general formula (II) wherein Z is $NR^1$ and $R^1$ is $CH_2CHF_2$, x is sulphur, n is 1 and $R^2$ is as listed in Table 1.

TABLE 11

Table 11 comprises 121 compounds or general formula (II) wherein Z is oxygen, X is oxygen, n is 1 and $R^2$ is as listed in Table 1, except that it is not an optionally substituted phenyl group.

TABLE 12

Table 12 comprises 121 compounds of general formula (II) wherein Z is oxygen, X is sulphur, n as 1 and $R^2$ is as listed in Table 1.

TABLE 13

Table 13 comprises 121 compounds of general formula (II) wherein Z is sulphur, X is oxygen, n is 1 and $R^2$ is as listed in Table 1.

TABLE 14

Table 14 comprises 121 compounds of general formula (II) wherein Z is sulphur, X is sulphur, n is 1 and $R^2$ is as listed in Table 1.

TABLE 15

Table 15 comprises 121 compounds of general formula (II) wherein Z is $NR^1$ and $R^1$ is $CH_2C\equiv CH$, X is oxygen, n is 1 and $R^2$ is as listed in Table 1.

TABLE 16

Table 16 comprises 121 compounds of general formula (II) wherein Z is $NR^1$ and $R^1$ is $CH_2C\equiv CH$, X is sulphur, n is 1 and $R^2$ is as listed in Table I.

TABLES 17 TO 32

Each of Tables 17 to 32 comprises 121 compounds of general formula (II) and respectively take the values of Z, X and $R^2$ in Tables 1 to 16. For all of Tables 17 to 32 n is 0.

TABLES 23 TO 64

Each of Tables 33 to 64 comprises 121 compounds of general formula (IX) and respectively take the values of Z, X, $R^2$ and n in Tables 1 to 32.

TABLES 65 TO 96

Each of Tables 65 to 96 comprises 121 compounds of general formula (X) and respectively take the values of Z, X, $R^2$ and n in Tables 1 to 32.

TABLE 97

Table 97 comprises 121 compounds of general formula (II) wherein Z is $NR^1$ and $R^1$ is benzyl, X is oxygen, n is 1 and $R^2$ is as listed in Table 1.

TABLE 98

Table 98 comprises 121 compounds of general formula (II) wherein Z is $NR^1$ and $R^1$ is benzyl, X is sulphur, n is 1 and $R^2$ is as listed in Table 1.

TABLE 99

Table 99 comprises 121 compounds of general formula (II) wherein Z is $NR^1$ and $R^1$ is $CO.CH_3$, X is oxygen, n is 1 and $R^2$ is as listed in Table 1.

TABLE 100

Table 100 comprises 121 compounds of general formula (II) wherein Z is $NR^1$ and $R^1$ is $CO.CH_3$, X is sulphur, n is 1 and $R^2$ is as listed in Table 1.

TABLE 101

Table 101 comprises 121 compounds of general formula (II) wherein Z is $NR^1$ and $R^1$ is $CH_2CH=CH_2$, is oxygen, n is 1 and $R^2$ is as listed in Table 1.

TABLE 102

Table 102 comprises 121 compounds of general formula (II) wherein Z is $NR^1$ and $R^1$ is $CH_2CH=CH_2$, X is sulphur, n is 1 and $R^2$ is as listed in Table 1.

TABLES 103 TO 108

Each of Tables 103 to 108 comprises 121 compounds of general formula (II) and respectively take the values of Z, X and $R^2$ in Tables 97 to 102. For all of Tables 103 to 108 n is 0.

TABLES 109 TO 120

Each of Tables 109 to 120 comprises 121 compounds of general formula (IX) and respectively take the values of Z, X, $R^2$ and n in Tables 97 to 108.

TABLES 121 TO 132

Each of Tables 121 to 122 comprises 121 compounds of general formula (X) and respectively take the values of Z, X, $R^2$ and n in Tables 97 to 108.

TABLE 133

Table 133 comprises compounds of formula (II) wherein n is 1, X is 0 and Z is $NR^1$, and $R^1$ and $R^2$ join to form a ring optionally bearing substituents.

TABLE I

| Compound No. | $NR^1R^2$ form |
|---|---|
| 1 | indole |
| 2 | piperidine |
| 3 | morpholine |
| 4 | thiomorpholine |
| 5 | indoline |
| 6 | pyrrolidine |
| 7 | azetidine |

Table I shows melting point or selected proton NMR data obtained at 270 MHz for certain compounds described in Tables 1 to 133. Chemical shifts are measured at 20° C. unless otherwise stated and are in parts per million from tetramethylsilane. At 20° C. certain compounds interconvert between two rotameric forms slowly, giving rise to a poorly defined spectrum and two sets or signals for certain parts of the molecule. Deuterochloroform was used as solvent unless otherwise stated. The following abbreviations are used:

| | br = broad | t = triplet |
|---|---|---|
| | s = singlet | q = quartet |
| | d = doublet | m = multiplet |
| | td = triplet of doublets | ppm = parts per million |
| | brs = broad singlet | brm = broad multiplet |
| Compound No. (Table) | | |
| 2 (1) | 3.7(3H, s), 3.8(3H, s), 5.1(2H, s), 6.85(1H, brs), 7.6(1H, s), 7.1–7.8(8H, m) ppm. | |
| 3 (1) | 3.7(3H, s), 3.3(3H, s), 5.1(2H, s), 6.85(1H, brs), 7.6(1H, s), 6.9–7.6(7H, m), 8.1(1H, t) ppm. | |
| 4 (1) | 3.7(3H, s), 3.8(3H, s), 4.4(2H, d), 5.0(3H, brs), 7.1–7.4(8H, m), 7.4(1H, m), 7.6(1H, s) ppm. | |
| 5 (1) | 74–78° C.. | |
| 6 (1) | 151–153° C.. | |
| 7 (1) | 3.7(3H, s), 3.8(3H, s), 2.3(3H, s), 5.1(2H, s), 6.6–7.5(9H, m), 7.6(1H, s) ppm. | |
| 8 (1) | 3.7(3H, s), 3.3(3H, s), 5.1(2H, s), 6.8(2H, m), 7.0(1H, m), 7.1–7.5(2H, m), 7.6(1H, s) ppm. | |
| 10 (1) | 2.45(3H, s), 3.68(3H, s), 3.81(3H, s), 5.11(2H, s), 6.62(1H, brs), 6.94(1H, d), 7.02–7.08(1H, m), 7.15–7.24(2H, m), 7.30–7.40(3H, m), 7.44–7.50(1H, m), 7.60(1H, s) ppm. | |
| 12 (1) | 92–93° C.. | |
| 15 (1) | 115–118° C.. | |

-continued

| | |
|---|---|
| br = broad | t = triplet |
| s = singlet | q = quartet |
| d = doublet | m = multiplet |
| td = triplet of doublets | ppm = parts per million |
| brs = broad singlet | brm = broad multiplet |

| Compound No. (Table) | |
|---|---|
| 16 (1) | 3.7(3H, s), 3.3(3H, s), 3.8(3H, s), 5.1(2H, s), 6.8–7.0(3H, m), 7.1–7.5(5H, m), 7.6(1H, s), 8.1(1H, m)ppm. |
| 18 (1) | 62–64° C.. |
| 20 (1) | 3.7(3H, s), 3.3(3H, s), 5.0(2H, s) 5.1–5.3(2H, m), 5.8(1H, m), 7.1–7.5(6H, m), 7.6(1H, s) ppm. |
| 23 (1) | 3.69(3H, s), 3.82(3H, s), 5.13(2H, s), 6.17(1H, brs), 6.91–6.96(2H,t), 7.11–7.21(2H, m), 7.30–7.37(2H, m), 7.42–7.48(1H, m), 7.59(1H, s) ppm. |
| 24 (1) | 57–59° C. |
| 27 (1) | 3.7(3H, s), 3.85(3H, s), 5.15(2H, s), 6.6–6.7(1H, m), 6.85–7.05(2H, m), 7.2(1H, m), 7.35(2H, m), 7.45(1H, m), 7.6(1H, s), 7.9(1H, m) ppm. |
| 28 (1) | 113–115° C.. |
| 29 (1) | 91–93° C.. |
| 32 (1) | 3.7(3H, s), 3.8(3H, s), 3.9(3H, s), 5.1(2H, s), 6.7(1H, d), 7.1–7.5(5H, m), 7.6(1H, s), 8.1(1H.d) ppm. |
| 33 (1) | 48–50° C.. |
| 104 (1) | 107–109° C.. |
| 105 (1) | 114–116° C.. |
| 2 (2) | 3.3(3H, s), 2.65(3H, s), 3.8(3H, s), 5.1(2H, s), 7.1–7.5(8H, m), 7.6(1H, s) ppm. |
| 3 (2) | 3.25(3H, s), 3.65(3H, s), 3.8(2H, s), 5.1(2H, m), 7.0–7.4(8H, m), 7.55(1H, s) ppm. |
| 5 (2) | 3.3(3H, s), 3.6(3H, s), 3.8(2H, s), 5.1(2H, s), 7.1–7.4(9H, m), 7.6(1H, s) ppm. |
| 6 (2) | 3.4(3H, s), 3.65(3H, s), 3.8(3H, s), 5.1(2H, s), 7.1–7.4(4H, m), 7.5(1H, t), 7.6(1H, s), 7.7(1H, m), 8.05(1H, m), 8.2(1H, t)ppm. |
| 8 (2) | 3.3(3H, s), 3.7(3H, s), 3.8(3H, s), 5.1(2H, s), 6.9–7.4(8H, m), 7.6(1H, s) ppm. |
| 10 (2) | 2.41(3H, s), 3.29(3H, s), 3.66(3H, s), 3.80(3H, s), 5.08(2H, s), 7.00–7.17(4H, m), 7.21–7.36(4H, m), 7.56(1H, s) ppm. |
| 12 (2) | 84–87° C.. |
| 13 (2) | 3.3(3H, s), 3.65(3H, s), 3.8(3H, s), 5.1(2H, s), 6.95–7.4(8H, m), 7.55(1H, s) ppm. |
| 15 (2) | 3.33(3H, s), 3.62+3.71(3H, s+s), 3.78+3.84(3H, s+s), 4.75–5.00+5.10(2H, brs, s), 6.97–7.10(1H, m), 7.15–7.67(7H, m), 7.94–8.01(1H, m) ppm. |
| 16 (2) | 3.2(3H, s), 3.65(3H, s), 3.8(3H, s), 5.0–5.1(2H, brm), 6.9–7.4(8H, m), 7.5(1H, s) ppm. |
| 18 (2) | 3.17–3.25(3H, s+s), 3.63–3.72(3H, s+s), 3.78–3.84(3H, s+s), 4.81–5.18(2H, 3×d), 6.88–7.24(3H, m), 7.28–7.74(6H, m) ppm. |
| 21 (2) | 119–121° C.. |
| 23 (2) | 3.21+3.25(3H, s+s), 3.65+3.71(3H, s+s), 3.79+3.83(3H, s+s), 5.03+5.15(2H, s+s), 6.91–6.98(2H, t), 7.05–7.30(4H, m), 7.32–7.41+7.49–7.54(1H, m+m), 7.55+7.59(1H, s+s) ppm. |
| 24 (2) | 3.2(3H, s), 3.7(3H, s), 3.8(3H, s), 5.2(2H, s), 6.8–7.0(2H, m), 7.0–7.4(5H, m), 7.55(1H, s) ppm. |
| 27 (2) | 3.25(3H, s), 3.67(3H, s), 3.8(3H, s), 5.1(2H, s), 6.9–7.4(7H, m), 7.55(1H, s) ppm. |
| 28 (2) | 3.25(3H, s), 3.7(3H, s), 3.8(3H, s), 5.05(2H, s), 6.3–6.5(2H, m), 6.85–7.4(5H, m), 7.55(1H, s) ppm. |
| 29 (2) | 3.35(3H, s), 3.67(3H, s), 3.71(3H, s), 5.11(2H, brs), 7.05–7.40(6H, m), 7.55–7.71(3H, m) ppm. |
| 33 (2) | NMR run in deuterodimethylsulphoxide at 100° C.. 3.2(3H, s), 3.6(3H, s), 3.75(3H, s), 3.8(3H, s), 4.9(2H, s), 7.0–7.7(7H, m), 7.6(1H, s), 7.85(1H, m) ppm. |
| 60 (2) | 3.45(3H, s), 3.7(3H, s), 3.8(3H, s), 5.15(2H, s), 7.6(1H, s), 7.0–7.8(7H, m), 8.4(1H, m) ppm. |
| 104 (2) | 3.25(3H, s), 3.65(2H, s), 3.8(3H, s), 5.1(2H, s), 7.0–7.4(7H, m) 7.55(1H, s) ppm. |
| 105 (2) | 3.3(3H, s), 3.65(2H, s), 3.8(3H, s), 5.1(2H, s), 7.1–7.4(5H, m), 7.6(1H, m), 7.6(1H, s), 8.0(1H, m) ppm. |
| 106 (2) | 3.3(3H, s), 3.65(3H, s), 3.8(3H, s), 5.1(2H, s), 7.1–7.4(5H, m), 7.55(1H, s), 8.1–8.3(2H, m) ppm. |
| 3 (3) | 1.1(3H, t), 3.6–3.75(5H, m), 3.8(3H, s), 5.05(2H, s), 7.0–7.4(8H, m), 7.55(1H, s) ppm. |
| 5 (3) | 1.15(2H, t), 3.65(3H, s), 3.75(2H, q), 3.8(3H, s), 5.1(2H, s), 7.1–7.4(9H, m), 7.6(1H, s) ppm. |
| 6 (3) | 1.1(3H, t), 3.7(3H, s), 3.8(2H, q), 3.8(3H, s), 5.1(2H, s), 7.1–7.7(6H, m), 7.6(1H, s), 8.1(2H, m) ppm. |
| 13 (3) | 1.1(3H,t), 3.65(3H, s), 3.7(2H, q), 3.8(3H, s), 5.05(2H, s), 7.0–7.4(8H, m ), 7.55(1H, s) ppm. |

-continued

| | |
|---|---|
| br = broad | t = triplet |
| s = singlet | q = quartet |
| d = doublet | m = multiplet |
| td = triplet of doublets | ppm = parts per million |
| brs = broad singlet | brm = broad multiplet |

| Compound No. (Table) | |
|---|---|
| 23 (3) | 78–80° C.. |
| 24 (3) | 1.09–1.15(3H, t), 3.65(5H, brs), 3.80(3H, s), 5.00–5.15(2H, s), 6.82–6.93(2H, m), 7.00–7.43(5H, m), 7.55(1H, s) ppm. |
| 27 (3) | 1.15(3H, t), 3.7(5H, m), 3.85(3H, s), 5.05(2H, s), 6.9–7.4(7H, m), 7.55(1H, s) ppm. |
| 28 (3) | 1.15(3H, t), 3.65(3H, s), 3.67(2H, q), 3.8(3H, s), 5.05(2H, s), 6.9–7.35(7H, m), 7.55(1H, s) ppm. |
| 104 (3) | 1.15(3H, t), 3.65(3H, s), 3.7(2H, q), 3.8(3H, s), 5.05(2H, s), 7.0–7.4(7H, m,), 7.55(1H, s) ppm. |
| 105 (3) | 1.15(3H, t), 3.7(3H, s), 3.75(2H, q), 3.85(3H, s), 5.1(2H, s), 7.1–7.55(6H, m), 7.58(1H, s), 7.95(1H, m) ppm. |
| 106 (3) | 1.15(3H, t), 3.65(3H, s), 3.7(2H, q), 3.8(3H, s), 5.1(2H, s), 7.1–7.4(5H, m), 7.55(1H, s), 8.2(2H, m) ppm. |
| 5 (4) | 0.9(3H, t), 1.5–1.7(2H, m), 3.6–3.7(2H, m), 3.7(3H, s), 3.8(3H, s), 5.1(2H, s), 7.0–7.4(9H, m), 7.6(1H, s) ppm. |
| 6 (5) | 3.7(3H, s), 3.8(3H, s), 4.0(2H, td), 5.1(2H, s), 6.1(1H, t, J=58Hz), 7.55(1H, s), 7.1–7.7(6H, m), 8.1–8.2(2H, m) ppm. |
| 2 (6) | 3.6(3H, s), 3.8(3H, s), 5.5(2H, s), 7.2(1H, m), 7.3–7.5(7H, m), 7.6(1H, s), 8.2(1H, brs) ppm. |
| 5 (6) | 3.6(3H, s), 3.57(3H, s), 5.5(2H, s), 7.1–7.5(9H, m), 7.6(1H, s), 8.2(1H, brs) ppm. |
| 7 (6) | 100–102° C.. |
| 8 (6) | 3.7(3H, s), 3.8(3H, s), 5.5(2H, s), 6.8–7.5(8H, m), 7.6(1H, s), 8.2(1H, s) ppm. |
| 9 (6) | 171–174° C.. |
| 11 (6) | 50° C. |
| 21 (6) | 2.4(3H, s), 3.65(3H, s), 3.8(3H, s), 5.5(2H, s), 7.1–7.4(8H, m), 7.6(1H, s), 8.8(1H, brs) ppm. |
| 5 (12) | 93–95° C.. |
| 16 (15) | 102–103° C.. |
| 1 (17) | 137–139° C.. |
| 4 (17) | 82–84° C.. |
| 5 (17) | 167–169° C.. |
| 24 (17) | 111–113° C.. |
| 5 (18) | 3.35(3H, s), 2.55(3H, s), 3.70(3H, s), 7.13–7.41(9H, m), 7.46(1H, s) ppm. |
| 24 (18) | 3.28(3H, s), 3.52(3H, s), 3.71(3H, s), 6.84–6.94(2H, m), 7.15–7.35(5H, m), 7.42(1H, s) ppm. |
| 3 (65) | 138–139° C.. |
| 5 (65) | 147–149° C.. |
| 3 (66) | 2.87–2.92(3H, d), 3.22(3H, s), 3.93(3H, s), 4.98(2H, brs), 6.78(1H, brs), 7.07–7.54(8H, m) ppm. |
| 5 (66) | 2.88–2.91(3H, d), 3.29(3H, s), 3.94(3H, s), 5.01(2H, s), 6.78(1H, br, s), 7.15–7.29(3H, m), 7.31–7.40(5H, m) ppm. |
| 8 (97) | 3.65(3H, s), 3.8(3H, s), 4.9(3H, s), 5.1(2H, s), 6.9(3H, m), 7.1–7.35(10H, m), 7.55(1H, s) ppm. |
| 12 (99) | 2.66(3H, s), 3.68(3H, s), 3.72(3H, s), 5.00–5.16(2H, q), 6.90–6.94(1H, d), 7.08–7.12(1H, m), 7.15–7.39(5H, m), 7.46–7.52(1H, m), 7.56(1H, s)ppm. |
| 23 (101) | 102–103° C.. |
| 1 (133) | 3.6(3H, s), 3.75(3H, s), 5.35(2H, s), 6.55(1H, d), 7.2–7.6(8H, m), 7.6(1H, s), 3.15(1H, m) ppm. |
| 2 (133) | 76–78° C.. |
| 3 (133) | 62–64° C.. |
| 4 (133) | 82–85° C.. |
| 5 (133) | 121–123° C.. |

Compounds of the present invention can be prepared as shown in Schemes I and II. Throughout Schemes I and II the variables n, $R^1$, $R^2$, Z and X have the values given above and V is W (which is as defined above) or a group which can be converted into W (such as $CH_2CO_2H$, $CH_2CO_2CH_3$, $CO.CO_2CH_3$, $(CH_3O)_2CHCHCO_2CH_3$ or $HO.CH=CCO_2CH_3$). When V is not W then methods for converting it into W include those described in EP-A-0242081, EP-A-0254426 and EP-A-0398692 (the later showing the conversion of $W=CH_3O.N=CCO_2CH_3$ into $W=CH_3.N=CCONHCH_3$). Methods for converting V, when it is not W, into W are selected for their compatibility with the functional groups present.

A compound of formula (Ia) can be prepared by treating a chloroformate or chlorothionoformate of formula (VI) wherein V, X and n are as defined above, with a compound of formula $HZR^2$, wherein Z and $R^2$ are as defined above, in a suitable solvent (such as toluene or dichloromethane) and in the presence of a suitable base (such as pyridine or triethylamine).

A chloroformate or chlorothionoformate of formula (VI) wherein V, X and n are as defined above, can be prepared b reacting a compound of formula (III), wherein V and n are as defined above, with phosgene or thiophosgene in a suitable solvent (such as toluene or dichloromethane) in the presence of a suitable base (such as pyridine).

A compound of formula (Ia), wherein Z is $NR^1$, can alternatively be prepared from a carbonate of general formula (VII), wherein $R^6$ is not aliphatic (which, when V is W, is a compound of formula (I) wherein Z and X are oxygen) in a suitable solvent (such as N,N-dimethylformamide) optionally in the presence of a suitable base (such as sodium hydride) with a suitable amine of type $R^1R^2NH$, wherein $R^1$ and $R^2$ are as defined above.

A compound of formula (VII), can be prepared by treating an alcohol of formula (III) with a chloroformate of formula (VIII), wherein $R^6$ is an aryl or heteroaryl optionally bearing substituents, in a suitable solvent (such as toluene or zichloromethane) in the presence of a suitable base (such as pyridine or 4-N,N-dimethylaminopyridine).

Chloroformates of general formula (VIII) are known in the art or can be made by adapting literature procedures (H. E. Carter, R. L. Frank and H. W; Johnston, *Org. Synth.* collective volume III page 167, or W. L. Haas, E. V. Knumkains and K. Gerzon. *J.Am.Chem.Soc.*, (1966), 88, page 1988.)

A compound of formula (V) (wherein Z is $NR^1$ and $R^1$ is not hydrogen, and wherein V, n, $R^2$ are as defined above and X is oxygen) can be prepared by alkylating a compound of formula (IV) which, when V is W, is a compound of formula (I)), wherein Z is $NR^1$ and $R^1$ is hydrogen, and wherein V, n, X and $R^2$ are as defined above, with a compound of formula $R^1L$, wherein $R^1$ is not hydrogen and L is a leaving group (such as a halogen atom or a sulphate or sulphonate group) in the presence of a suitable base (such as potassium or sodium carbonate, potassium or sodium hydroxide or sodium hydride) in a suitable solvent (such as N,N-dimethylformamide or dimethylsulphoxide).

A compound of formula (IV) can be prepared by treating an alcohol of formula (III), wherein V and n are as defined above, with an isocyanate of formula $R^2NCO$ (wherein $R^2$ is as defined above) or an isothiocyanate of formula $R^2NCS$ (wherein $R^2$ is as defined above), in a suitable solvent (such as dichloromethane or diethyl ether) and optionally in the presence of a suitable base (such as pyridine or 4-N,N-dimethylaminopyridine).

The isocyanates of formula $R^2NCO$ and isothiocyanates of formula $R^2NCS$ are either known in the art or can be made by adapting standard literature methods [see for example, 'Advanced Organic Chemistry', Jerry March, 3rd edition (1985), page 1166, Wiley-Interscience, and references cited therein].

The alcohols of formula (III) are either known in the art or can be made by adapting standard literature methods (GB 2189485 or EP-A2-0398692).

A compound of formula (Ia), (IV) or (V), wherein V is W, is a compound of formula (I).

In a further aspect, the present invention provides processes for preparing compounds of formula (I), and the intermediate (E)-methyl 3-methoxy-2-[2-((4-nitrophenoxy)carbonyloxymethyl)phenyl]propenoate.

The present invention also relates to a process for the preparation of oxime ether amides which are useful intermediates for the preparation of compounds of formula (X).

According to the present invention there is provided a process for the preparation of a compound of formula (XX), wherein p is 0 or 1, the process comprising reacting a compound of formula (XXIII), wherein p is 0 or 1, with methylamine.

In one particular aspect the present invention provides a process for the preparation of a compound of formula (XX), wherein p is 0 or 1, the process comprising the steps:

(a) reacting a compound of formula (XXII), wherein p is 0 or 1, with a methylating agent, in the presence of a base (for example an alkali metal carbonate or hydroxide or sodium hydride) to form a compound of formula (XXIII), wherein is 0 or 1; and, (b) reacting the compound of formula (XXIII), wherein p is 0 or 1, with methylamine.

In a further aspect the present invention provides a process for the preparation of a compound of formula (XX), wherein p is 0 or 1, the process comprising the steps:

a) reacting a compound of formula (XXI), wherein p is 0 or 1, with an alkyl nitrite in the presence of an acid or base to produce a compound of formula (XXII), wherein p is 0 or 1;

b) reacting the compound of formula (XXII), wherein p is 0 or 1, with a methylating agent in the presence of a base to form a compound of formula (XXIII), wherein p is 0 or 1; and, c) reacting the compound of formula (XXIII), wherein p is 0 or 1, with methylamine.

The present invention provides steps (a), (b) and (c) individually or in combination.

In another aspect the present invention provides a process for the preparation of a compound of formula (XX), wherein p is 0 or 1, the process comprising the steps:

a) reacting a compound of formula (XXI), wherein p is 0 or 1, with an alkyl nitrite in the presence of an acid (for example hydrogen chloride) or a base (for example an alkali metal alkoxide) to produce a compound of formula (XXII), wherein p is 0 or 1;

b) reacting the compound of formula (XXII), wherein p is 0 or 1, with a methylating agent, in the presence of a base (for example an alkali metal carbonate or hydroxide or sodium hydride) to form a compound of formula (XXIII), wherein p is 0 or 1; and c) reacting the compound of formula (XXIII), wherein p is 0 or 1, with methylamine.

Steps (a) and (b) above can be combined to give a "one-pot" process. Therefore, in a further aspect, the present invention provides a process for the preparation of a compound of formula (XX), wherein p is 0 or 1, the process comprising the steps of:

i) treating a compound of formula (XXI) with a base (for example an alkali metal alkoxide);

ii) treating the product of (i) with an alkyl nitrite;

iii) treating the product of (ii) with a methylating agent to form a compound of formula (XXIII); and, iv) reacting the compound of formula (XXIII), wherein p is 0 or 1, with methylamine.

In a further aspect the present invention provides a process for the preparation of a compound of formula (XXIV), wherein Y is chlorine or bromine, and p is 1, the process comprising reacting a compound of formula (XX) with a chlorinating or brominating agent.

In a still further aspect the present invention provides a process for the preparation of a compound of formula (XXIV), wherein Y is chlorine or bromine and p is 1, the process comprising the steps:

a) reacting a compound of formula (XXIII), wherein, p is 1, with methylamine to produce a compound of formula (XX), wherein p is 1; and, b) reacting the compound of formula (XX), wherein p is 1, with a chlorinating or brominating agent.

In another aspect the present invention provides a process for the preparation of a compound of formula (XXIV), wherein p is 1, and Y is chlorine or bromine, the process comprising the steps:

(a) reacting a compound of formula (XXII), wherein p is 1, with a methylating agent, in the presence of a base (for example an alkali metal carbonate or hydroxide or sodium hydride) to form a compound of formula (XXIII), wherein p is 1;

(b) reacting the compound or formula (XXIII), wherein p is 1, with methylamine to produce a compound of formula (XX), wherein p is 1; and, (c) reacting the compound of formula (XX), wherein p is 1 with a chlorinating or brominating agent.

In yet another aspect the present invention provides a process for the preparation of a compound or formula (XXIV), wherein p is 1 and Y is chlorine or bromine, the process comprising the steps:

a) reacting a compound of formula (XXI), wherein p is 1, with an alkyl nitrate in the presence of an acid or base to produce a compound of formula (XXII), wherein p is 1;

b) reacting the compound of formula (XXII), wherein p is 1, with a methylating agent in the presence of a base to form a compound of formula (XXIII), wherein p is 1;

c) reacting the compound of formula (XXIII), wherein p is 1, with methylamine to produce a compound of formula (XX), wherein p is 1; and, d) reacting the compound of formula (XX), wherein p is 1 with a chlorinating or brominating agent.

The alkyl moiety of an alkyl nitrite is a straight or branched chain and preferably contains from 1 to 10, (for example from 4 to 8) carbon atoms, and is, for example, a tert-butyl or iso-amyl moiety.

Alkali metals include sodium or potassium.

The alkoxide moiety is especially $C_{1-4}$ alkoxide, for example methoxide, ethoxide or tert-butoxide.

Methylating agents are compounds of formula $CH_3L$, wherein L is a leaving group (for example halogen), and are, for example, methyl iodide or dimethyl sulphate.

It is preferred that the present invention provides a process for the preparation of a compound or formula (XX) wherein p is 1.

A compound of formula (XX) can be prepared by reacting a compound of formula (XXIII) with methylamine in a suitable solvent (such as methanol or ethanol).

A compound of formula (XXIII) can be prepared by treating a compound of formula (XXII) with a suitable base (such as sodium or potassium carbonate or hydroxide or sodium hydride) and a methylating agent (such as methyl iodide or dimethyl sulphate) in a suitable solvent (such as N,N-dimethylformamide).

Alternatively, a compound of formula (XXIII) can be prepared by treating a compound of formula (XXI) with a base (such as potassium tert-butoxide) in a suitable solvent (such as tert-butanol), treating this mixture with an alkyl nitrite (such as tert-butyl nitrite) and then adding a methylating agent (such as methyl iodide or dimethyl sulphate) to the reaction mixture.

A compound of formula (XXII) can be prepared by treating a compound of formula (XXI) with a base (such as sodium methoxide) in a suitable solvent (such as methanol) in the presence of an alkyl nitrite (for example tert-butyl nitrite).

Alternatively, a compound of formula (XXII) can be prepared by treating a compound of formula (XXI) with an acid (such as hydrogen chloride) in a suitable solvent (such as methanol or ethanol) in the presence of an alkyl nitrite (for example tert-butyl nitrite).

A compound of formula (XXIV) wherein p is 1 can be prepared by treating a compound of formula (XX) wherein p is 1 with a suitable chlorinating or brominating agent (for example a combination of either carbon tetrabromide or carbon tetrachloride and triphenylphosphine) in a suitable solvent (such as 1,2-dichloroethane or tetrahydrofuran).

Compounds of formula (XXI) are known in the literature.

Compound of formula (XX), wherein p is 1, is known and is used in EP-A2-0398692 as an intermediate for fungicides.

In another aspect the present invention provides the intermediate compounds of formulae (XX), wherein p is 0, and (XXII), (XXIII) and (XXIV) wherein p is 0 or 1.

The compounds of formula (I) are active fungicides and may be used to control one or more of the following pathogens: *Pyricularia oryzae* on rice and wheat and other Pyricularia spp. on other hosts.

*Puccinia recondita, Puccinia striiformis* and other rusts on wheat, *Puccinia hordei, Puccinia striiformis* and other rusts on barley, and rusts on other hosts e.g. turf, rye, coffee, pears, apples, peanuts, sugar beet, vegetables and ornamental plants.

*Erysiphe graminis* (powdery mildew) on barley, wheat, rye and turf and other powdery mildews on various hosts such as *Sphaerotheca macularis* on hops, *Sphaerotheca fuliginea* on cucurbits (e.g. cucumber), *Podoschaera leucotricha* on apple and *Uncinula necator* on vines.

Cochliobolus spp., Helminthosporium spp., Drechslera spp. (Pyrenophora spp.), Rhynchosporium spp., Septoria spp. (including *Mycosphaerella graminicola* and *Leptosphaeria nodorum*), *Pseudocercosporella herpotrichoides* and *Gaeumannomyces graminis* on cereals (e.g. wheat, barley, rye), turf and other hosts.

*Cercospora arachidicola* and *Cercosporidium personatum* on peanuts and other Cercospora species on other hosts, for example, sugar beet, bananas, soya beans and rice.

*Botrytis cinerea* (grey mould) on tomatoes, strawberries, vegetables, vines and other hosts and other Botrytis spp. on other hosts.

Alternaria spp. on vegetables (e.g. cucumber), oil-seed rape, apples, tomatoes, cereals (e.g. wheat) and other hosts.

Venturia spp. (including *Venturia inaequalis* (scab)) on apples, pears, stone fruit, tree nuts and other hosts.

Cladosporium spp. on a range of hosts including cereals (e.g. wheat).

Monilinia spp. on stone fruit, tree nuts and other hosts.

Didymella spp. on tomatoes, turf, wheat and other hosts.

Phoma spp. on oil-seed rape, turf, rice, potatoes, wheat and other hosts.

Aspergillus spp. and Aureobasidium spp. on wheat, lumber and other hosts.

Ascochyta spp. on peas, wheat, barley and other hosts.

*Plasmopara viticola* on vines. Other downy mildews such as *Bremia lactucae* on lettuce, Peronospora spp. on soybeans, tobacco, onions and other hosts, *Pseudoperonospora humuli* on hops and *Pseudoperonospora cubensis* or cucurbits.

Pythium spp. on turf and other hosts.

*Phytophthora infestans* on potatoes and tomatoes and other Phytophthora spp. on vegetables, strawberries avocado, pepper, ornamentals, tobacco, cocoa and other hosts.

*Thanatephorus cucumeris* on rice and turf and other Rhizoctonia species on various hosts such as wheat and barley, vegetables, cotton and turf.

Sclerotinia spp. on turf, peanuts, oil-seed rape and other hosts.

Sclerotium spp. on turf, peanuts and other hosts.

Colletotrichum spp. on a range of hosts including turf, coffee and vegetables.

*Laetisaria fuciformis* on turf.

Mycosphaerella spp. on banana, peanut, citrus, pecan, papaya and other hosts.

Diaporthe spp. on citrus, soybean, melon, pear, lupin and other hosts.

Elsinoe spp. on citrus, vines, olives, pecans, roses and other hosts.

Pyrenopeziza spp. on oil-seed rape and other hosts.

*Oncobasidium theobromae* on cocoa causing vascular streak dieback.

Fusarium spp., Typhula spp., *Microdochium nivale*, Ustilago spp., Urocystis spp., Tilletia spp., and *Claviceps purpurea* on a variety of hosts but particularly wheat, barley, turf and maize.

Ramularia spp. on sugar beet and other hosts.

Post-harvest diseases particularly of fruit (e.g. *Pencillium digitatum* and *P. italicum* and *Trichoderma viride* on oranges, *Colletotrichum musae* and *Gloeosporium musarum* on bananas and *Botrytis cinerea* on grapes).

Other pathogens on vines, notably *Eutypa lata, Guignardia bidwellii, Phellinus igniarus, Phomopsis viticola, Pseudopezicula tracheiphila* and *Stereum hirsutum*.

Other pathogens on lumber, notably *Cephaloascus fragrans*, Ceratocystis spp., *Ophiostoma piceae*, Penicillium spp., *Trichoderma pseudokoningii, Trichoderma viride Trichoderma harzianum, Aspergillus niger, Leotographium lindbergi* and *Aureobasidium pullulans*.

Fungal vectors of viral diseases e.g. *Polymyxa graminis* on cereals as the vector of barley yellow mosaic virus (BYMV).

Some of the compositions snow a broad range of activities against fungi in vitro.

Further, some of the compositions may be active as seed dressings against pathogens including Fusarium spp., Septoria spp., Tilletia spp., (e.g. bunt, a seed-borne disease of wheat), Ustilago spp. and Helminthosporium spp. on cereals. *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor. It is preferred that all compositions, both solid and liquid formulations, comprise 0.0001 to 95%, more preferably 1 to 85%, for example 1 to 25% or 25 to 60%, of a compound as hereinbefore defined.

When applied the foliage of plants, the compounds of the invention are applied at rates of 0.1 g to 10 Kg, preferably 1 g to 8 Kg, more preferably 10 g to 4 Kg, of active ingredient (invention compound) per hectare.

When used as seed dressings, the compounds of the invention are used at rates of 0.0001 g (for example 0.001 g or 0.05 g) to 10 g, preferably 0.005 g to 8 g, more preferably 0.005 g to 4 g, of active ingredient (invention compound) per kilogram of seed.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic, systemic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of water dispersible powders or water dispersible granules comprising wetting or dispersing agents to facilitate the dispersion in liquids. The powders and granules may also contain fillers and suspending agents.

The compositions may also be in the form of soluble powders or granules, or in the form of solutions in polar solvents.

Soluble powders may be prepared by mixing the active ingredient with a water-soluble salt such as sodium bicarbonate, sodium carbonate, magnesium sulphate or a polysaccharide, and a wetting or dispersing agent to improve water dispersibility/solubility. The mixture may then be ground to a fine powder. Similar compositions may also be granulated to form water-soluble granules. Solutions may be prepared by dissolving the active ingredient in polar solvents such as ketones, alcohols and glycol ethers. These solutions may contain surface active agents to improve water dilution and prevent crystallisation in a spray tank.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Aqueous suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the uptake, distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives, for example, certain mineral oil and natural plant oil (such as soya bean and rape seed oil) additives, or blends of them with other adjuvants.

The invention compounds can be used as mixtures with fertilisers (e.g. nitrogen-, potassium- or phosphorus-containing fertilisers). Compositions comprising only granules of fertiliser incorporating, for example coated with, a compound of formula (I) are preferred. Such granules suitably contain up to 25% by weight of the compound. The invention therefore also provides a fertiliser composition comprising a fertiliser and the compound of general formula (I) or a salt or metal complex thereof.

Water dispersible powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts or aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and tri-isopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, alkyl glucosides, polysaccharides and the lecithins and the condensation products of the said partial esters with ethylene oxide. Suitable suspending agents are hydropholic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 1–85%, for example 1–25% or 25–60%, by weight of the active ingredient. After dilution to form aqueous preparations, such preparations may contain varying amounts of the active ingredient depending upon the intended purpose, but an aqueous preparation containing 0.0001 to 10%, for example 0.005 to 10%, by weight of active ingredient may be used.

The compositions of this invention may contain other compounds having biological activity, e.g. compounds having similar or complementary fungicidal activity or which possess plant growth regulating, herbicidal or insecticidal activity.

An additional fungicidal compound may be present in the composition of the invention. By including another fungicide, the resulting composition can have a broader spectrum of activity or a greater level of intrinsic activity than the compound of general formula (I) alone. Further the other fungicide can have a synergistic errect on the fungicidal activity of the compound of general formula (I). Examples of fungicidal compounds which may be included in the composition of the invention are (Z)-cis-1-(4-chlorophenyl)-2-(1H-1,2,4-triazol-1-yl)cycloheptanol, (2RS,3RS)-1-|3-(2-chlorophenyl)-2-(4-fluorophenyl) oxiran-2-ylmethyl|-1H-1,2,4-triazole, (RS)-1-aminopropylphosphonic acid, (RS)-4-(4-chlorophenyl)-2-phenyl-2-(1H-1,2,4-triazol-1-ylmethyl)butyronitrile, (Z)-N-but-2-enyloxymethyl-2-chloro-2',6'-diethylacetanilide, 1-(2-cyano-2-methoxyiminoacetyl)-3-ethyl urea, 3-(2,4-dichlorophenyl)-2-(1H-1,2,4-triazol-1-yl)quinazolin-4(3H)-one, 4-(2,2-difluoro-1,3-benzodioxol-4-yl)-pyrrole-3-carbonitrile, 4-bromo-2-cyano-N,N-dimethyl-6-trifluoromethylbenzimidazole-1-sulphonamide, 5-ethyl-5,8-dihydro-8-oxo(1,3)-dioxol-(4,5-g)quinoline-7-carboxylic acid, α-|N-(3-chloro-2,6-xylyl)-2-methoxyacetamido|-γ-butyrolactone, N-(2-methoxy-5-pyridyl)-cyclopropane carboxamide, (E)-methyl 2-|2-(6-(2-cyanophenoxy) pyrimidin-4-yloxy)phenyl|-3-methoxypropenoate, alanycarb, aldimorph, ampropylfos, anilazine, azaconazole, benalaxyl, benomyl, biloxazol, binapacryl, bitertanol, blasticidin S, bromuconazole, bupirimate, butenachlor, buthiobate, captafol, captan, carbendazim carbendazim chlorhydrate, carboxin, chinomethionate chlorbenzthiazone, chloroneb, chlorothalonil chlorozolinate, clozylacon, copper containing compounds such as copper oxychloride, copper oxyquinolate, copper sulphate and Bordeaux mixture, cycloheximide, cymoxanil cyproconazole, cyprofuram, di-2-pyridyl disulphide 1,1'-dioxide, dichiofluanid, dichlone, diclobutrazol, diclomezine dicloran, didecyl dimethyl ammonium chloride diethofencarb, difenoconazole, O,O-di-iso-propyl-S-benzy thiophosphate, dimefluazole, dimetconazole dimethomorph, dimethirimol, diniconazole, dinocap dipyrithione, ditalimfos, dithianon, dodemorph, dodine doguadine, edifenphos, epoxiconazole, etaconazole ethirimol, ethoxyquin, ethyl (Z)-N-benzyl-N-(|methy (methyl-thioethylideneamino-oxycarbonyl)amino|thio)-β alaninate, etridiazole, fenaminosulph, fenapanil, fenarimol fenbuconazole, fenfuram, fenpicionil, fenpropidin fenpropimorph, fentin acetate, fentin hydroxide, ferbam ferimzone, fluazinam, fluoroimide, flutolanil, flutriafol flusilazole, folpet, fuberidazole, furalaxyl, furconazole-cis guazatine, hexaconazole, hydroxyisoxazole, hymexazole imazalil, imibenconazole, ipconazole, iprobenfos iprodione, isopropanyl butyl carbamate, isoprothiolane, kasugamycin, mancozeb, maneb, mepanipyrim, mepronil, metalaxyl, methfuroxam, metiram, metiram-zinc, metsulfovax, myclobutanil, neoasozin, nickel dimethyldithiocarbamate, nitrothal-isopropyl, nuarimol, ofurace, organomercury compounds, oxadixyl, oxolinic acid, oxycarboxin, pefurazoate, penconazole, pencycuron, phenazin oxide, phosetyl-Al, phosphorus acids, phthalide, polyoxin D, polyram, probenazole, prochloraz, procymidone, propamocarb, propamocarb hydrochloride, propiconazole, propineb, propionic acid, prothiocarb, pyracarbolid, pyrazophos, pyrifenox, pyroquilon, pyroxyfur, pyrrolnitrin, quaternary ammonium compounds, quinconazole, quinomethionate, quintozene, rabenazole, sodium pentachlorophenate, streptomycin, sulphur, tebuconazole, techlofthalam, tecnazene, tetraconazole, thiabendazole, thicarbanil, thicyofen, 2-(thiocyanomethylthio)benzothiazole, thiophanate-methyl, thiram, timibenconazole, tolclofos-methyl, tolylfluanid, triacetate salt of 1,1'-iminodi(octamethylene)diguanidine, triadimefon, triadimenol, triazbutyl, triazoxide, tricyclazole, tridemorph, triforine, triflumizole, triticonazole, validamycin A, vapam, vinclozolin, zineb and ziram. The compounds of general formula (I) can be mixed with soil, peat or other rooting media for the protection of plants against seed-borne, soil-borne or foliar fungal diseases.

The following Examples illustrate the invention. Where they are used in the Examples, DISPERSOL and TWEEN are Trade Names or Trade Marks. Where shown, infrared (IR) and NMR data are selective; no attempt has been made to list every absorption in all cases. The following abbreviations are used throughout:

| m.p. = melting point | m = multiplet |
| s = singlet | brs = broad singlet |
| d = doublet | dt = doublet of triplets |

EXAMPLE 1

This Example illustrates the preparation of (E)-methyl 3-methoxy-2-|2-((methyl)(phenyl)carbamoyloxymethyl) phenyl|propenoate (Compound No. 5 of Table 2).

(E)-Methyl 2-|2-(bromomethyl)phenyl|-3-methoxypropenoate (15 g) was dissolved in acetone (200 ml) and the solution was cooled to 2° C. A solution of silver nitrate (22.35 g) in water (200 ml) at 4° C. was added to this. The temperature rose to 12° C. After stirring for 40 minutes the green/grey precipitate which had formed was filtered off and the filtrate partitioned between water and diethyl ether. The diethyl ether layer was washed with brine, dried over anhydrous sodium sulphate and evaporated under reduced pressure to give an oil which was purified by chromatography on silica gel, eluting with diethyl ether, to give (E)-methyl 2-|2-(hydroxymethyl)phenyl|-3-methoxypropenoate as a viscous oil (6.33 g, 54%). $^1$H NMR (CDCl$_3$): 2.3(t,1H), 3.7(s,3H) 3.8(s,3H), 4.5(d,2H), 7.1(m,1H), 7.2–7.4(m,2H), 7.5(m,1H), 7.6(s,1H) ppm.

A solution of (E)-methyl 2-|2-(hydroxymethyl)phenyl|-3-methoxypropenoate (1 g) in toluene (10 ml) was added slowly to a solution of phosgene in toluene (12.5 w/w, 6.5 ml). After stirring for 3 hours, water (70 ml) was added and the resulting mixture was extracted with diethyl ether. The diethyl ether extract was washed with brine, dried over anhydrous sodium sulphate and evaporated under reduced pressure to leave an oil. The oil was purified by chromatography on silica gel, eluting with 30% ethyl acetate/hexane to give (E)-methyl 2-|2-(chloroformyloxymethyl) phenyl|-3-methoxypropenoate (0.163 g, 13%). $^1$H NMR (CDCl$_3$): 3.7(s,3H), 3.8(s,3H), 4.5(s,2H), 7.1–7.5(m,4H), 7.6(s,1H) ppm. IR (film): 1631, 1707, 1774 cm$^{-1}$.

To a solution of (E)-methyl 2-|2-(chloroformyloxymethylphenyl|-3-methoxypropenoate (0.16 g) in dichloromethane (5 ml) was added N-methylaniline (0.13 ml) and 4-N,N-dimethylaminopyridine. The resulting mixture was stirred at room temperature for 3 hours after which time it was partitioned between water and dichloromethane. The organic layer was separated, dried over anhydrous sodium sulphate and evaporated under reduced pressure to leave an oil which was purified by chromatography on silica gel, eluting with diethyl ether:hexane 7:3, to give the title compound as an oil (0.153 g, 77%).

EXAMPLE 2

This Example illustrates the preparation of (E)-methyl 3-methoxy-2-|2-((3-trifluoromethylphenyl) carbamoyloxymethyl)phenyl|-propenoate (Compound No. 2, Table I).

To a solution of (E)-methyl 2-|2-(hydroxymethyl)phenyl| -3-methoxypropenoate (0.2 g) in toluene (10 ml) were added 3-trifluoromethylphenyl isocyanate (0.14 ml) and 4-N,N-dimethylaminopyridine (0.12 g). The resulting mixture was stirred for 2 hours after which time water (10 ml) was added and the resulting mixture stirred for 1½ hours. The mixture was partitioned between water and diethyl ether. The organic layer was dried over anhydrous sodium sulphate and evaporated under reduced pressure to leave an oil. This was purified by chromatography on silica gel, eluting with ethyl acetate:hexane 3:7, to give the title compound as a gum (0.366 g, 91%).

EXAMPLE 3

This Example illustrates the preparation of (E)-methyl 3-methoxy-2 -|2-((phenyl)carbamoyloxymethyl)phenyl| propenoate (Compound No. 5, Table 1).

(E)-Methyl 2-|2-(hydroxymethyl)phenyl|-3-methoxypropenoate (0.256 g) was dissolved in dichloromethane (5 ml). Phenyl isocyanate (140 µl) and 4-N,N-dimethylaminopyridine (28 mg) were added to the reaction. After stirring at room temperature for 2½ hours the reaction was diluted with water (10 ml). The organic layer was separated off and the aqueous phase extracted with dichloromethane (2×10 ml). The combined extracts were dried (anhydrous sodium sulphate) and concentrated to give a gum. Chromatography on silica gel, eluting with 25% ethyl acetate/hexane, gave the title compound as a gum which crystallised on standing (m.p. 74°–78° C., yield 0.384 g, 98%).

EXAMPLE 4

This Example illustrates the preparation of (E)-methyl 3-methoxy-2-[-2-((phenyl)(n-propyl)carbamoyloxymethyl) phenyl|propenoate (Compound No. 5, Table 4).

A solution of (E)-methyl 3-methoxy-2-|2-((phenyl) carbamoyloxymethyl)phenyl|propenoate (0.51 g) |prepared as described in Example 3 above|, in N,N-dimethylformamide (5 ml) was added dropwise to a suspension of sodium hydride (66 mg of a 60% dispersion in oil which had been washed with 40–60 petrol) in N,N-dimethylformamide (2 ml). After stirring the resulting mixture at room temperature for 30 minutes, 1-iodopropane (0.28 g) in N,N-dimethylformamide (2 ml) was added slowly. The resulting mixture was stirred at room temperature for 4 hours and then allowed to stand overnight. The mixture was then poured into water and extracted with diethyl ether three times. The combined extracts were washed with water three times, dried over magnesium sulphate and evaporated under reduced pressure to leave a gum. The gum was purified by chromatography on silica gel, eluting with diethyl ether:hexane 2:1, to give the title compound as a colourless gum (0.18 g, 31%).

EXAMPLE 5

This Example illustrates the preparation of (E)-methyl 2-[2-((benzoyl) carbamoyloxy)phenoxy]-3-methoxypropenoate (Compound No. 1 of Table 17).

(E)-Methyl 2-[2-hydroxyphenyl]-3-methoxypropenoate (2 g) was dissolved in benzoylisocyanate (1.41 g) and zoluene (2 ml). The mixture was cooled to 0° C. and a solution of 4-N,N-dimethylaminopyridine (1.18 g) in toluene (2 ml) was added dropwise. After stirring at room temperature overnight the resulting white precipitate was filtered off and washed with toluene to give the title compound.

EXAMPLE 6

This Example illustrates the preparation of (E)-methyl 3-methoxy-2-[2-((4-nitrophenoxy)carbonyloxymethyl)phenyl]propenoate.

A solution of (E)-methyl 2-[2-(hydroxymethyl)phenyl]-3-methoxypropenoate (0.55 g) in dichloromethane (5 ml) was added dropwise to a stirred solution of 4-nitrophenylchloroformate (0.5 g) in dichloromethane (20 ml) at room temperature. 4-N,N-Dimethylaminopyridine (0.3 g) was then added to the reaction mixture in small portions. After stirring at room temperature for 1½ hours the reaction mixture was poured into water (50 ml) and extracted twice with diethyl ether (75 ml). The solvent was dried with magnesium sulphate and evaporated under reduced pressure to give a yellow gum. Purification by chromatography on silica gel, eluting with diethyl ether gave the title compound as a yellow gum (0.71 g, 74%); $^1$H NMR: 3.7(3H,s), 3.85(3H,s), 5.2(2H,s), 7.2–7.6(6H,m), 7.6(1H,s), 8.3(2H,m) ppm).

EXAMPLE 7

This Example illustrates the preparation of (E)-methyl 3-methoxy-2-[2-((methyl)(pyridin-2-yl)carbamoyloxymethyl)phenyl]propenoate (Compound No. 60 of Table 2).

(E)-Methyl 3-methoxy-2-[2-((4-nitrophenoxy)carbonyloxymethyl)phenyl]-propenoate (0.35 g, prepared as described in Example 6) dissolved in N,N-dimethylformamide (5 ml) was added dropwise to a solution of 2-(N-methylamino)pyridine (0.11 g) and pyridine (0.1 ml) in N,N-dimethylformamide (15 ml) at room temperature. The reaction mixture was stirred at room temperature for 1½ hours and then heated to 100° C. for 4 hours before cooling to room temperature. The mixture was poured into water (50 ml) and extracted with diethyl ether (3×50 ml). The combined organic layers were washed twice with water (50 ml), dried over magnesium sulphate and evaporated under reduced pressure to give a dark brown oil. Chromatography on silica gel, eluting with 1:9 (hexane:diethyl ether) gave the product as a pink gum (60 mg, 29%).

EXAMPLE 8

This Example illustrates the preparation of N-methyl-2-(2-hydroxymethylphenyl)-2-methoxyiminoacetamide.

Step 1

A solution of sodium methoxide (5.5 mmol) in methanol (5 ml) was added to a stirred solution of 3-isochromanone (0.74 g) and tert-butyl nitrite (1.55 g) in methanol (10 ml) under an atmosphere of nitrogen at room temperature. The temperature rose from 19° C. to 23° C. After stirring at room temperature for 3 hours the methanol was removed under reduce pressure. The resulting residue was dissolved in water (15 ml), filtered to remove insoluble matter and acidified with 2M hydrochloric acid (3 ml). The brown precipitate formed was filtered off to give a pale brown solid (0.41 g, 46%). Extraction of the aqueous solution with ethyl acetate gave a further 0.14 g of impure product. The pale brown solid and impure product were together recrystallised from ethyl acetate to give isochroman-3,4-dione 4-oxime as a pale brown solid (0.14 g, m.p. 181°–185° C.); $^1$H NMR (d$^6$-DMSO) δ 5.35(s,2H), 7.3(m,1H), 7.45(m,2H), 8.45(m, 1H), 12.9(brs,1H) ppm.

Step 2

Isochroman-3,4-dione 4-oxime (3.27 g) was dissolved in N,N-dimethylformamide at 0° C. Potassium carbonate (2.55 g) was added to the reaction mixture over 5 minutes. A solution of dimethyl sulphate (1.75 ml) in N,N-dimethylformamide (5 ml) was added to the reaction mixture. After stirring for 4 hours at 0° C. the reaction mixture was poured into water and extracted three times with diethyl ether. The combined organic layers were washed three times with water, dried over magnesium sulphate and concentrated to a red oil (2.03 g). The combined aqueous layers were extracted three times with ethyl acetate and the organic extracts dried over magnesium sulphate. The solvent was removed under reduced pressure to give a further 0.52 g of a red oil. The combined samples of red oil were purified using a column of silica gel eluting with diethyl ether/hexane (3:1) to give isochroman-3,4-dione 4-O-methyloxime as a solid (1.15 g, m.p. 84°–85° C.); $^1$H NMR (CDCl$_3$) δ 4.2(s,3H), 5.35(s,2H), 7.3(m,1H), 7.45(m,2H) 8.3(m,1H) ppm.

Step 3

Isochroman-3,4-dione 4-O-methyloxime (1.08 g) was dissolved in tetrahydrofuran and a solution of methylamine in ethanol (2.5 ml of a 35% W/V solution) was added in one portion. After stirring at room temperature for 1½ hours the reaction mixture was concentrated under reduced pressure to give a brown solid. Recrystallisation from ethyl acetate gave the title compound as a white solid (0.86 g, 68%). $^1$H NMR (CDCl$_3$) δ 2.95(d,3H), 3.2(t,1H), 3.95(s,3H), 4.41(d,2H) 6.95(brs,1H), 7.1(d,1H), 7.4(dt,2H), 7.5(d,1H) ppm.

EXAMPLE 9

This Example illustrates the preparation of N-methyl-2 (2-bromomethylphenyl)-2-methoxyiminoacetamide.

Carbon tetrabromide (0.33 g) was added to a solution o N-methyl-2-(2-hydroxymethylphenyl)-2-methoxyiminoacetamide (0.11 g) and triphenylphosphine (0.26 g) in tetrahydrofuran (10 ml) at 0° C. The reaction mixture was stirred at 0° C. for 1½ hours and then at room temperature for 1 hour. The reaction mixture was then poured into water and extracted three times with ethyl acetate. The combined extracts were washed with brine and dried over magnesium sulphate. The solution was the concentrated under reduced pressure to leave a gum. Col umn chromatography (eluting with diethyl ether on silic gel) gave the N-methyl-2-(2-bromomethylphenyl)-2 methoxyiminoacetamide as a gum (80 mg, 57%). $^1$H NMI (CDCl$_3$) δ 2.95(d,3H), 4.0(s,3H), 4.35(s,2H), 6.8(brs,1H 7.1–7.5(m,4H) ppm.

EXAMPLE 10

This Example illustrates the preparation of (E)-methyl 3-methoxy-2-|2-(morpholinocarbamoyloxymethyl)phenyl| propenoate (Compound No. 3 of Table 133).

(E)-,methyl 3-methoxy-2-|2-((4-nitrophenoxy) carbamoyloxymethyl)phenyl|-propenoate (0.3 g, prepared as described in Example 6) was dissolved in N,N-dimethylformamide (10 ml) and morpholine (70 mg) was added dropwise at room temperature under an atmosphere of nitrogen. The reaction mixture was stirred for 2 hours and then poured into water (50 ml). The products were extracted into diethyl ether (2×50 ml) which was washed with water (50 ml) and dried over magnesium sulphate. The solvent was removed at reduced pressure to give a clear gum. Column chromatography on silica gel, eluting with diethyl ether, gave the title compound (0.1 g) as a clear oil which solidified on standing. m.p. 62°–64° C.

EXAMPLE 11

This Example illustrates the preparation of (E)-N-methyl 2-|2-((2-fluorophenyl)carbamoyloxymethyl)phenyl| methoxyiminoacetamide (Compound No. 3 of Table 65).

(E)-N-Methyl 2-|2-(hydroxymethyl)phenyl| methoxyiminoacetamide (0.39 g), 2-fluorophenyl isocyanate (0.29 g) and 4-N,N-dimethylaminopyridine (73 mg) were dissolved in dichloromethane (10 ml) at room temperature and stirred or 3 hours. After standing overnight, the reaction solution was chromatographed directly on silica gel using diethyl ether as eluent to give the title compound as a white solid (0.60 g) m.p. 138°–139° C.

EXAMPLE 12

This Example illustrates the preparation of (E)-N-methyl 2-|2-((methyl)(2-fluorophenyl)carbamoyloxymethyl) phenyl|methoxyiminoacetamide (Compound No. 3 of Table 66).

A dispersion of sodium hydride (60% in oil, 40 mg, 1 mmol) was washed with 40–60 petrol and then suspended in dry N,N-dimethylformamide (2 ml). (E)-N-Methyl 2-|2-((2-fluorophenyl)carbamoyloxymethyl)phenyl| methoxyiminoacetamide (0.36 g, prepared as described in Example 11) in dry N,N-dimethylformamide (10 ml) was added to the reaction mixture dropwise over 5 minutes and then allowed to stir at room temperature for 20 minutes. A solution of methyl iodide (0.14 g) in dry N,N-dimethylformamide (2 ml) was added dropwise to the reaction mixture which was then left for 2 hours. The solution was poured into water and extracted with diethyl ether (x3). The combined organic phases were washed with water and dried with magnesium sulphate. The solvent was removed at reduced pressure to give a gum (0.33 g). Column chromatography on silica gel, eluting with diethyl ether, gave the title compound as a colourless gum (0.28 g). IR (film) 3359 cm$^{-1}$, 1708 cm$^{-1}$ and 1665 cm$^{-1}$.

EXAMPLE 13

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous DISPERSOL T or as a solution in acetone or acetone/ethanol which was diluted to the required concentration immediately before use. The formulations (100 ppm active ingredient) were sprayed on to the foliage or applied to the roots of the plants in the soil. The sprays were applied to maximum retention and the root drenches to a final concentration equivalent to approximately 40 ppm a.i. in dry soil. TWEEN 20 was added to give a final concentration of 0.05% when the sprays were applied to cereals.

For most of the tests the compounds were applied to the soil (roots) or to the foliage (by spraying) one or two days before the plant was inoculated with the disease. An exception was the test on Erysiphe graminis in which the slants were inoculated 24 hours before treatment. Foliar pathogens were applied by spray as zoosporangial suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease level present (i.e. leaf area covered by actively sporulating disease) on each of the treated plants was recorded using the following assessment scale:

| | |
|---|---|
| 0 = 0% disease present | 20 and 24 = 10.1–20% disease present |
| 1 = 0.1–1% disease present | 30 = 20.1–30% disease present |
| 3 = 1.1–3% disease present | 60 = 30.1–60% disease present |
| 5 = 3.1–5% disease present | 90 and 94 = 60.1–100% disease present |
| 10 = 5.1–10% disease present | |

Each assessment was then expressed as a percentage of the level of disease present on the untreated control plants. This calculated value is referred to as a POCO (Percentage of Control) value. An example of a typical calculation is as follows:

Disease level on untreated control=90
Disease level on treated plant=30

$$POCO = \frac{\text{disease level on treated plant}}{\text{disease level on untreated control}} \times 100 = \frac{30}{90} \times 100 = 33.3$$

This calculated POCO value is then rounded to the nearest of the values in the 9-point assessment scale shown above. In this particular example, the POCO value would be rounded to 30. If the calculated POCO falls exactly mid-way between two of the points, it is rounded to the lower of the two values.

The results are shown in Table II.

TABLE II

| Compound No. (Table) | Erysiphe graminis tritici (Wheat) | Septoria nodorum (Wheat) | Puccinia recondita (Wheat) | Plasmopara viticola (Vines) | Phytophthora infestans (Tomatoes) | Pyricularia oryzae (Rice) | Venturia inaequalis (Apples) | Thanatephorus cucumeries (Rice) |
|---|---|---|---|---|---|---|---|---|
| 2 (1) | 60 | 20 | 10 | 10 | 10 | 5 | 0 | 60 |
| 3 (1) | 0 | 0 | 0 | 0 | 30 | 90 | 1 | 90 |
| 4 (1) | 90 | 30 | 30 | 20 | 60 | 90 | 60 | 90 |

TABLE II-continued

| Compound No. (Table) | Erysiphe graminis tritici (Wheat) | Septoria nodorum (Wheat) | Puccinia recondita (Wheat) | Plasmopara viticola (Vines) | Phytophthora infestans (Tomatoes) | Pyricularia oryzae (Rice) | Venturia inaequalis (Apples) | Thanatephorus cucumeries (Rice) |
|---|---|---|---|---|---|---|---|---|
| 5 (1) | 60 | 30 | 60 | 5 | 60 | 10 | 30 | 60 |
| 6 (1) | 90 | 30 | 90 | 90 | 60 | 90 | 60 | 90 |
| 7 (1) | 5 | 90 | 10 | 60 | 90 | 0 |  | 60 |
| *8 (1) | 60 | 90 | 0+ | 90 | 90 | 10 | 0 | 90 |
| *10 (1) | 90 | 90 | 90+ | 90 | 90 |  | 0 | 90 |
| 12 (1) | 0 | 10 | 10+ | 0 | 30 | 5 | 0 | 30 |
| 15 (1) |  | 0 | 90+ | 0 | 3 | 5 | 0 |  |
| 16 (1) | 90 | 90 | 90+ | 0 | 90 | 20 | 60 | 90 |
| 18 (1) | 90 | 90 | 90+ | 0 | 90 | 60 | 3 | 90 |
| 20 (1) | 20 | 90 | 3+ | 90 | 60 | 20 | 5 | 90 |
| 23 (1) | 0 | 30 | 30+ | 0 | 90 | 30 | 0 | 0 |
| 24 (1) | 0 | 60 |  | 0 | 20 | 90 | 0 | 60 |
| *27 (1) | 90 | 90 | 90+ | 90 | 90 | 30 | 90 | 90 |
| *28 (1) | 90 | 30 | 5+ | 30 | 90 | 0 | 60 | 90 |
| 29 (1) | 5 | 60 | 30+ | 20 |  | 0 | 0 | 5 |
| 32 (1) | 20 | 30 |  | 0 | 30 | 90 | 60 | 90 |
| 33 (1) | 60 | 90 |  | 90 | 90 | 90 | 0 | 90 |
| 104 (1) | 90 | 90 | 90+ | 60 | 90 | 90 | 90 | 90 |
| 105 (1) | 30 | 90 | 90+ | 90 | 90 | 60 | 20 | 60 |
| 2 (2) | 0 | 0 | 0 | 0 | 90 | 5 | 0 | 30 |
| 3 (2) | 0 | 0 |  | 0 | 0 | 0 | 0 | 0 |
| 5 (2) | 0 | 0 | 0 | 0 | 0 | 0 | 0 | 5 |
| 6 (2) | 0 | 0 |  | 0 | 10 | 0 | 0 | 30 |
| 8 (2) | 0 | 0 | 0+ | 0 | 0 | 0 | 0 | 0 |
| 10 (2) | 0 | 0 | 0+ | 0 | 20 | 0 | 0 | 20 |
| 12 (2) | 0 | 3 | 30+ | 0 | 5 | 10 | 0 | 0 |
| 13 (2) | 0 | 0 | 0+ | 0 | 0 | 0 | 0 | 0 |
| 15 (2) |  | 5 | 0+ | 0 | 60 | 0 | 0 |  |
| 16 (2) | 0 | 5 | 10+ | 0 | 20 | 0 | 1 | 5 |
| 18 (2) | 60 | 90 | 90+ | 3 | 90 | 60 | 3 | 60 |
| *21 (2) | 90 | 60 | 90+ | 0 | 90 | 30 | 60 | 90 |
| 23 (2) | 0 | 0 | 0+ | 0 | 0 | 0 | 0 | 0 |
| 24 (2) | 0 | 0 |  | 0 | 0 | 0 | 0 | 0 |
| 27 (2) |  | 0 | 0+ | 0 | 5 | 0 | 0 | 0 |
| 28 (2) | 0 | 0 | 0+ | 0 | 10 | 0 | 0 | 0 |
| 29 (2) | 0 | 30 | 20+ | 0 |  | 0 | 0 | 30 |
| 33 (2) | 0 | 90 | 90+ | 10 | 90 | 30 | 60 | 60 |
| *60 (2) | 3 | 90 | 90+ | 20 | 90 | 3 | 0 | 90 |
| 104 (2) | 0 | 0 | 0+ | 0 | 10 | 0 | 0 | 0 |
| 105 (2) | 0 | 90 | 90+ | 0 | 0 | 5 | 10 | 0 |
| 106 (2) | 0 | 30 | 30+ | 0 | 60 |  | 0 | 0 |
| 3 (3) | 0 | 0 |  | 0 | 0 | 0 | 0 | 0 |
| 5 (3) | 0 | 0 |  | 0 | 5 | 0 | 0 | 5 |
| 6 (3) | 0 | 0 |  | 0 | 10 | 0 | 0 | 90 |
| 13 (3) | 0 | 0 | 0+ | 0 | 0 | 0 | 0 | 0 |
| 23 (3) | 0 | 5 | 0+ | 0 | 5 | 1 | 0 | 0 |
| 24 (3) | 0 | 0 | 0+ | 0 | 60 | 10 | 0 | 0 |
| 27 (3) | 0 | 30 | 0+ | 0 | 20 | 0 | 0 | 0 |
| 28 (3) | 0 | 0 | 0+ | 0 | 20 | 1 | 0 | 0 |
| 104 (3) | 0 | 10 | 0+ | 0 | 10 |  | 0 | 0 |
| 105 (3) | 90 | 90 | 90+ | 0 | 0 | 60 | 0 | 20 |
| 106 (3) | 30 | 60 | 60+ | 0 | 90 |  | 0 | 0 |
| 5 (4) | 1 | 10 | 20 |  | 90 | 90 | 0 | 90 |
| *6 (5) | 20 | 90 | 90+ | 90 | 90 | 60 | 0 | 90 |
| 2 (6) | 60 | 60 | 30 | 30 | 60 | 5 | 3 | 90 |
| *5 (6) |  | 90 | 90 | 90 | 90 | 60 | 0 | 0 |
| *7 (6) | 0 | 90 | 0+ | 60 | 90 | 10 | 60 | 30 |
| *8 (6) | 90 | 90 | 90 | 60 | 90 | 30 | 60 | 90 |
| 9 (6) | 90 | 90 | 90 | 90 |  | 20 |  | 90 |
| 11 (6) |  | 60 | 20 | 0 |  | 20 |  | 90 |
| 21 (6) | 3 | 0 | 0 | 0 |  | 0 |  | 0 |
| *5 (12) | 60 | 90 | 90+ | 3 | 90 | 60 | 0 | 60 |
| 16 (15) | 0 | 10 | 60+ | 0 | 5 | 0 | 1 | 0 |
| 1 (17) | 94 | 94 | 24 | 24 | 24 | 94 | 0 |  |
| 4 (17) | 10 | 60 | 1 | 0 |  | 5 |  | 0 |
| 5 (17) | 60 | 60 |  | 0 | 60 | 5 | 1 | 90 |
| 24 (17) | 0 | 0 | 0+ | 0 | 0 | 0 | 0 | 60 |
| *24 (18) | 60 | 90 | 90+ | 90 | 90 | 90 | 90 | 90 |
| 3 (65) | 0 | 20 | 30+ | 30 | 90 | 3 | 1 | 60 |
| *5 (65) | 30 | 90 | 90+ | 90 | 90 | 30 | 90 | 90 |
| *3 (66) | 90 | 90 | 90+ | 90 | 90 | 60 | 30 | 90 |
| 5 (66) | 0 | 5 | 10+ | 0 | 0 | 0 | 0 | 0 |
| 8 (97) | 90 | 90 | 90+ | 0 | 90 | 30 | 30 | 90 |
| 12 (99) | 30 | 10 | 30+ | 0 | 90 | 10 | 5 | 90 |

TABLE II-continued

| Compound No. (Table) | Erysiphe graminis tritici (Wheat) | Septoria nodorum (Wheat) | Puccinia recondita (Wheat) | Plasmopara viticola (Vines) | Phytophthora infestans (Tomatoes) | Pyricularia oryzae (Rice) | Venturia inaequalis (Apples) | Thanatephorus cucumeries (Rice) |
|---|---|---|---|---|---|---|---|---|
| 23 (101) | 0 | 10 | 0+ | 0 | 90 | 0 | 0 | 0 |
| *1 (133) | 90 | 90 | 90+ | 0 | 90 | 90 | 30 | 60 |
| 2 (133) | 60 | 90 | 90+ | 5 | 90 | 20 | 5 | 90 |
| 3 (133) | 90 | 90 | 90+ | 90 | 90 | 90 | 60 | 90 |
| 4 (133) | 90 | 90 | 60+ | 0 | 90 | 90 | 10 | 60 |
| *5 (133) | 60 | 90 | 90+ | 90 | 90 | 90 | 90 | 90 |

*10 ppm foliar spray only
+Plants inoculated with *Puccinia recondita* 48 hours before treatment CHEMICAL FORMULAE
(in description)

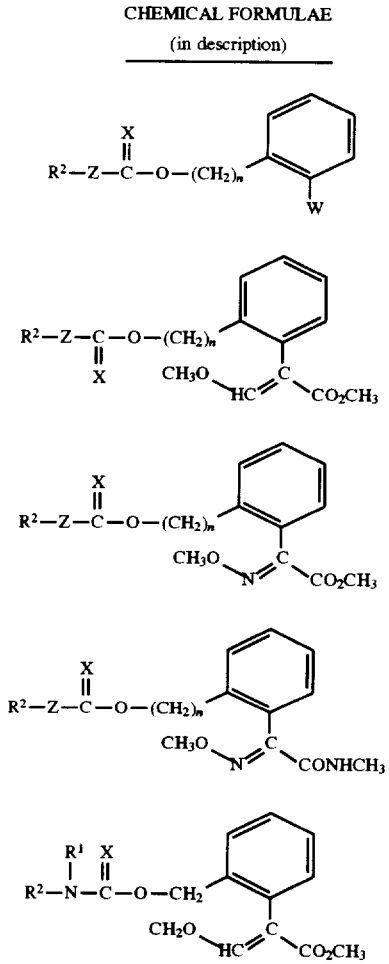

-continued
CHEMICAL FORMULAE
(in description)

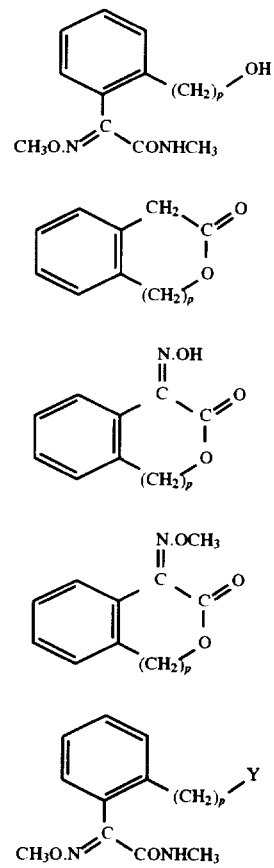

Scheme I

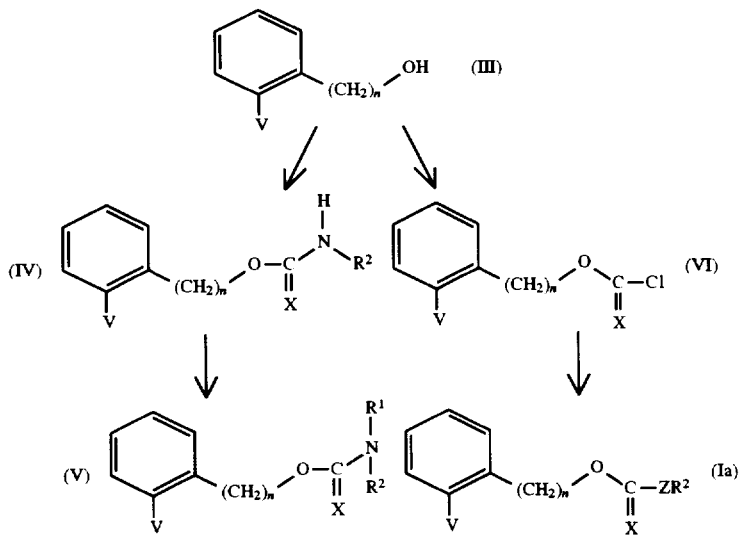

Scheme II

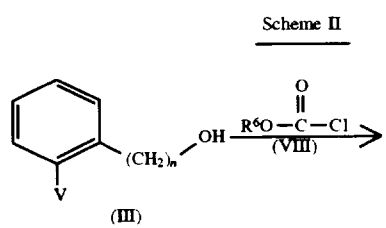

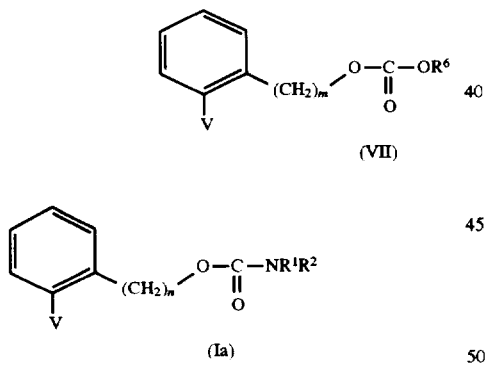

We claim:
1. A compound of formula (XX)

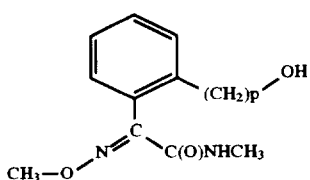

(XX)

wherein p is 0.

2. A compound of formula (XXIV)

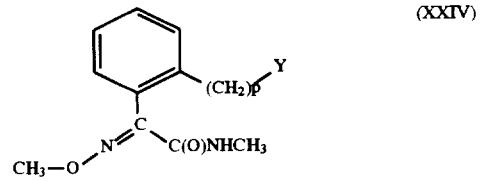

(XXIV)

wherein p is 1, and Y is chlorine or bromine.

3. A process for the preparation of a compound of formula (XX)

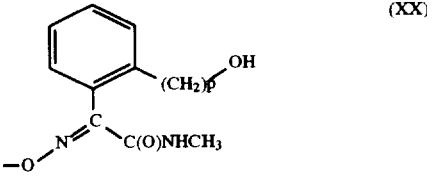

(XX)

wherein p is 0 or 1, comprising reacting a compound of formula (XXIII)

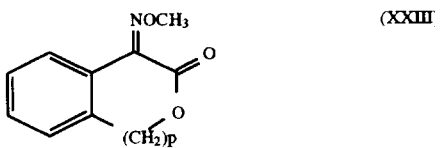

(XXIII)

wherein p is 0 or 1, with methylamine.

4. A process according to claim 3, comprising the further step of reacting a compound of formula (XXII)

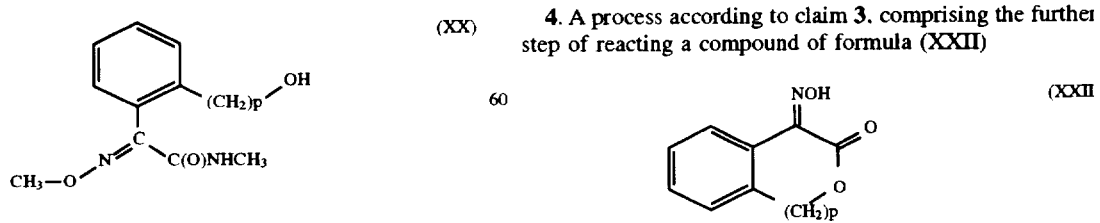

(XXII)

wherein p is 0 or 1, with a methylating agent in the presence of a base to form a compound of formula (XXIII)

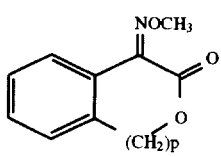

wherein p is 0 or 1.

5. A process according to claim 4, comprising the further step of reacting a compound of formula (XXI)

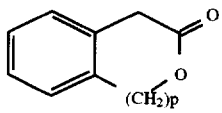

wherein p is 0 or 1, with an alkyl nitrite in the presence of an acid or base to produce a compound of formula (XXII)

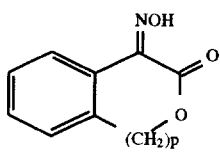

wherein p is 0 or 1.

6. A process for the preparation of a compound of formula (XXIV):

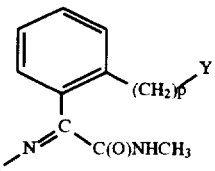

wherein p is 1, and Y is chlorine or bromine, the process comprising reacting a compound of formula (XX)

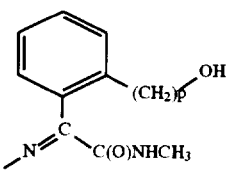

wherein p is 1, with a chlorinating or brominating agent.

* * * * *